US00RE47982E

(19) United States
(12) Reissued Patent
D'Acquisto et al.

(10) Patent Number: US RE47,982 E
(45) Date of Reissued Patent: May 12, 2020

(54) ANNEXIN 1 ANTIBODY

(71) Applicant: Queen Mary & Westfield College, University of London, London (GB)

(72) Inventors: Fulvio D'Acquisto, London (GB); Mauro Perretti, London (GB)

(73) Assignee: Queen Mary & Westfield College, University of London, London (GB)

(21) Appl. No.: 15/697,668

(22) Filed: Sep. 7, 2017

Related U.S. Patent Documents

Reissue of:
(64) Patent No.: 9,127,051
Issued: Sep. 8, 2015
Appl. No.: 13/702,593
PCT Filed: Jun. 9, 2011
PCT No.: PCT/GB2011/000876
§ 371 (c)(1),
(2) Date: Feb. 19, 2013
PCT Pub. No.: WO2011/154705
PCT Pub. Date: Dec. 15, 2011

(30) Foreign Application Priority Data

Jun. 9, 2010 (GB) ..... 1009675.8
Jul. 15, 2010 (GB) ..... 1011943.6

(51) Int. Cl.
*C07K 16/18* (2006.01)
*A61K 45/06* (2006.01)
*A61K 39/395* (2006.01)
*A61K 39/00* (2006.01)

(52) U.S. Cl.
CPC ..... *C07K 16/18* (2013.01); *A61K 39/3955* (2013.01); *A61K 45/06* (2013.01); *A61K 2039/505* (2013.01); *C07K 2317/76* (2013.01)

(58) Field of Classification Search
CPC ..... C07K 16/18; A61K 39/3955; A61K 45/06
See application file for complete search history.

(56) References Cited

U.S. PATENT DOCUMENTS

| | | | | |
|---|---|---|---|---|
| 5,051,364 | A * | 9/1991 | Isacke et al. | 530/388.24 |
| 5,162,311 | A | 11/1992 | Herrling et al. | |
| 5,565,338 | A | 10/1996 | Ishizaka | |
| 5,567,440 | A | 10/1996 | Hubbell et al. | |
| 2005/0113297 | A1 | 5/2005 | Francois et al. | |
| 2006/0024315 | A1* | 2/2006 | Schnitzer et al. | 424/155.1 |

FOREIGN PATENT DOCUMENTS

| | | | |
|---|---|---|---|
| CN | 1726395 | A | 12/2013 |
| WO | 2003057715 | | 7/2003 |
| WO | WO/03/057715 | * | 7/2003 |
| WO | 2005027965 | | 3/2005 |
| WO | 2005027965 | A1 | 3/2005 |
| WO | 2005117848 | | 12/2005 |
| WO | 2005117848 | A2 | 12/2005 |
| WO | 2007139813 | | 12/2007 |
| WO | 2010064012 | | 6/2010 |
| WO | 2010064012 | A2 | 6/2010 |
| WO | 2011154705 | | 12/2011 |
| WO | 2013088110 | | 6/2013 |
| WO | 2018146230 | | 8/2018 |

OTHER PUBLICATIONS

Bates et al., "Genetic immunization for antibody generation in research animals by intravenous delivery of plasmid DNA", BioTechniques, 2006, 40(2), pp. 199-207.
Final Office Action dated Apr. 19, 2019 cited in related U.S. Appl. No. 14/365,311.
S. D'Angelo et al., "Many Routes to an Antibody Heavy-Chain CDR3: Necessary, Yet Insufficient, for Specific Binding", Frontiers in Immunology, 2018, 9:1-13.
Alonso et al., "Animal models of obsessive-compulsive disorder: utility and limitations", Neuropsychiatric Disease and Treatment, 2015, 11, pp. 1939-1955.
Barderas et al., "Affinity maturation of antibodies assisted by in sillico modeling", PNAS 2008, 105(26), pp. 9029-9034.
Benros et al., "The epidemiologic evidence linking autoimmune diseases and psychosis", Biol Psychiatry, 2014, 75, pp. 300-306.
Bergink, et al., "Autoimmunity, inflammation, and psychosis: a search for peripheral markers", Biol Psyciatry, 2014, 75(4), pp. 324-331.
Bist et al., "Annexin-A1 regulates TLR-mediated IFN-beta production through an interaction with Tank-binding kinase 1", J Immunol, 2013, 191(8), pp. 4375-4382.
Bradyanova et al., Functional elimination of autoreactive T cells by antibody therapy in MRL/LPR murine model of systemic lupus erythematosus, Abstract AO4 in Proceedings of Vth Workshop on Experimental models and methods in biomedical research, Apr. 7-9, 2014, pp. 20.
Brod, et al., "As above, so below' examining the interplay between emotion and the immune system", Immunology, 2014, 143(3), pp. 311-318.
Brown et al., "Tolerance of single, but not multiple, amino acid replacements in antibody VH CDR 2: a means of minimizing B cell wastage from somatic hypermutation?", J Immuno, 1996, pp. 3285-3291.
Brynskikh, et al., Adaptive immunity affects learning behavior in mice, J Brain Behav Immun, 2008, 22(6), pp. 861-869.
Buckingham et al., "Lipocortin 1: a second messenger of glucocorticoid action in the hypothalamo-pituitary-adrenocortical axis", Molecular Medicine Today, 1997, 3(7), pp. 296-302.
Buckingham, "Stress and the neuroendocrine-immune axis: the pivotal role of glucorticoids and lipocortin 1", British Journal of Pharmacology, 1996, pp. 1-19.

(Continued)

*Primary Examiner* — Padmashri Ponnaluri
(74) *Attorney, Agent, or Firm* — Stradley Ronon Stevens & Young, LLP

(57) ABSTRACT

The present invention provides a specific binding molecule raised against the human Anx-A1 protein having the amino acid sequence shown in FIG. 2A. The present invention also relates to the sue of such a specific binding molecule in the treatment of T cell-mediated disease.

12 Claims, 20 Drawing Sheets

Figure 3B:
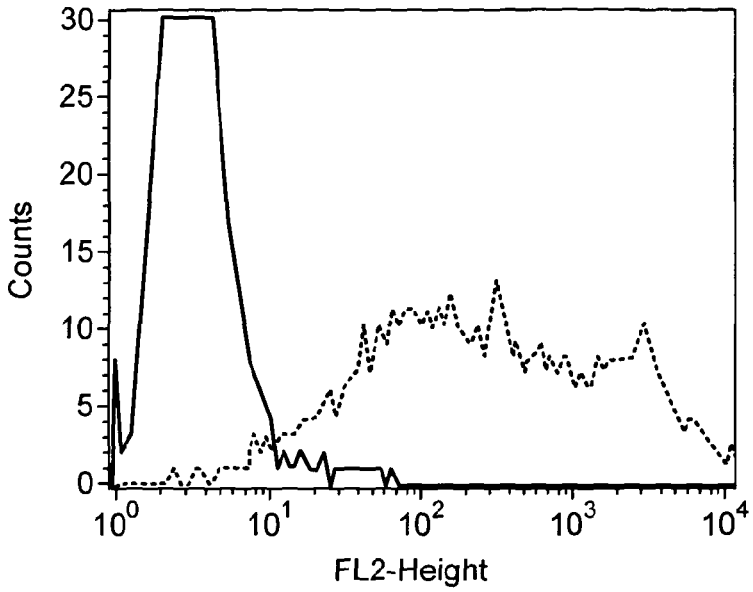

Specification includes a Sequence Listing.

(56) References Cited

OTHER PUBLICATIONS

Cai et al., "Preparation and identification of monoclonal antibody against annexin I", Zhongliu 2006, 26(11), pp. 979-983, English Abstract only.
Chipinski et al., Functional elimination of autoreactive T cells by antibody therapy in humanized SCID model of systemic lupus erythematosus, Abstract AO4 in Proceedings of Vth Workshop on Experimental models and methods in biomedical research, Apr. 7-9, 2014, pp. 19.
Clark et al., A proteome analysis of the anterior cingulate cortex gray matter in schizophrenia, Molecular Psychiatry, 2006, 11, pp. 459-470.
Correia et al., "Recurrent duplications of the annexin A1 gene (ANXA1) in autism spectrum disorders", Molecular Autism, 2014, 5(28), pp. 1-14.
Cui et al., "Overexpression of annexin a1 induced by terephthalic acid calculi in rat bladder cancer", Proteomics, 2007, 7(22), pp. 4192-4202.
D'Acquisto et al., "Annexin A1: a novel target of the immunosuppressive effects of glucocorticoids in autoimmune diseases", FASEN Journal, 2006, 20(5 (part 2)), pp. A1376.
D'Acquisto et al., "Annexin-1 modulates T-cell activation and differentiation", Blood, 2007, 109(3), pp. 1095-1102.
D'Acquisto et al., "Annexin-A1: a pivotal regulator of the innate and adaptive immune systems", Br J Pharmacol, 2008, 155(2), pp. 152-169.
D'Acquisto et al., "Glucocorticoid treatment inhibits annexin-1 expression in rheumatoid arthritis CD4+ T cells", Rheumatology, 2008, 47(5), pp. 636-639.
D'Acquisto et al., "Impaired T cell activation and increased Th2 lineage commitment in Annexin-1-deficient T cells", Eur J Immunol, 2007, 37(11), pp. 3131-3142.
D'Acquisto, "Editorial overview: Immunomodulation: Exploiting the circle between emotions and immunity: impact on pharmacological treatments", Curr Opin Pharmacol, 2016, 29, pp. 8-12.
D'Acquisto, "From the bench to the pipline: testing the immunosuppressive potential of novel therapies targeting annexin A1", Immunology, 2010, 131, pp. 159.
D'Acquisto, "Smile-It's in your blood!", Biochem Pharmacol, 2014, 91(3), pp. 287-292.
D'Acquisto, F., "On the adaptive nature of annexin-A1", Curr Opin Pharmacol, 2009, 9(4), pp. 521-528.
Dijkstra et al., "Multiple sclerosis: some possible therapeutic opportunities", Tips Reviews, 1993, 14, pp. 124-129.
Ellwardt et al., "Understanding the role of T cells in CNS homeostasis", Trends Immunol, 2016, 37(2), pp. 154-165.
Falini et al., "Simple diagnostic assay for hairy cell leukaemia by immunocytochemical detection of annexin A1 (ANXA1)", Lancet, 2004, 363(9424), pp. 1869-1870.
Ferlazzo et al., Anti-inflammatory effects of annexin-1: stimulation of IL-10 release and inhibition of nitric oxide synthesis, International Immunopharmacology, 2003, 3, pp. 1363-1369.
Flower et al., "Lipocortin-1: cellular mechanisms and clinical relevance", Trends Pharmacol Sci, 1994, 15(3), pp. 71-76.
Gao et al., "Reduced fear memory and anxiety-like behavior in mice lacking formylpeptide receptor 1", Behav Genet, 2011, 41, pp. 723-733.
Hayhoe et al., "Annexin 1 and its bioactive peptide inhibit neutrophil-endothelium interactions under flow: indication of distinct receptor involvement", Blood, 2006, 107(5), pp. 2123-2130.
Hong X., et al., "Hybridoma passage in vitro may result in reduced ability of antimannan antibody to protect against disseminated candidiasis", Infect Immun, 2006, 74(7), pp. 4310-4321.
Huggins, A., et al., "Annexin-1-deficient dendritic cells acquire a mature phenotype during differentiation", FASEB J, 2009, 23(4), pp. 985-996.
Huitinga, I., et al., "Effect of annexin-1 on experimental autoimmune encephalomyelitis (EAE) in the rat", Clin Exp Immunol, 1998, 111(1), pp. 198-204.
Iaccarino et al., "Anti-annexins autoantibodies: their role as biomarkers of autoimmune disease", Autoimmunity Reviews, 2011, 10(9), pp. 553-558.
Jacobs et al., "Role of IL-1 and IL-4 in exacerbations of murine antigen-induced arthritis", Immunology, 1994, 83(3), pp. 390-396.
John et al., "Annexin A1 and the formyl peptide receptor family: neuroendocrine and metabolic aspects", Current Opinion in Pharmacology, 2008, 8(6), pp. 765-776.
Kamaly et al., "Development and in vivo efficacy of targeted polymeric inflammation-resolving nanoparticles", PNAS, 2013, 110(16), pp. 6506-6511.
Kellner, "Drug treatment of obsessive-compulsive disorder", Dialogues Clin Neurosci, 2010, pp. 187-197.
Lim, L. H., et al., "Promoting detachment of neutrophils adherent to murine postcapillary venules to control Inflammation: effect of lipocortin 1", Proc Natl Acad Sci USA, 1998, 95(24), pp. 14535-14539.
Liu et al., "Identification of annexin A1 as a proinvasive and prognostic factor for lung adenocarcinoma", Clinical & Experimental Metastasis, 2011, 28(5), pp. 413-425.
Lupus erythematosus—Wikipedia. http://en.wikipedia.org/wiki/Lupus_erythematosus, Jun. 7, 2017, pp. 1-4.
Maderna, P., et al., "Modulation of phagocytosis of apoptotic neutrophils by supernatant from dexamethasone-treated macrophages and annexin-derived peptide Ac(2-26)", J Immunol, 2005, 174(6), pp. 3727-3733.
Maynard et al., "Protection against anthrax toxin by recombinant antibody fragments correlates with antigen affinity", Nature Biotech, 2002, 20(6), pp. 597-601.
Mihaylova et al., "Annexin A1 as a target for managing murine pristane-induced systemic lupus erythematosus", Autoimmunity, 2017, 50(4), pp. 257-268.
O'Kennedy et al., "Antibody engineering: an overview", Essays Biochem, 1991, 26, pp. 59-75.
Oliani et al., "Neutrophil interaction with inflamed postcapillary venule endothelium alters annexin 1 expression", Am J Pathol, 2001, 158, pp. 603-615.
Oliani, S. M., et al., "Annexin 1 localisation in tissue eosinophils as detected by electron microscopy", Mediators Inflamm, 2002, 11(5), pp. 287-292.
Owens et al., "The genetic engineering of monoclonal antibodies", J Immunol Methods, 1994, 168(2), pp. 149-165.
Final Office Action dated Apr. 2, 2019 from related U.S. Appl. No. 14/616,320, filed Feb. 6, 2015.
Final Office Action dated Jul. 16, 2018 in related U.S. Appl. No. 14/365,311.
Pakula et al., "Genetic analysis of protein stability and function", Annu Rev Genet, 1989, 23, pp. 289-310.
Paschalidis et al., "Role of endogenous Annexin-A1 in the regulation of thymocyte positive and negative selection", Cell Cycle, 2010, 9(4), pp. 785-794.
Paschalidis, N., et al., "Modulation of experimental autoimmune encephalomyelitis by endogenous annexin A1", J Neuroinflammation, 2009, 6, pp. 33.
Pepinsky, R. B., et al., "Monoclonal antibodies to lipocortin-1 as probes for biological function", FEBS Lett, 1990, 261(2), pp. 247-252.
Perretti et al., "Acute inflammatory responses in the mouse: exacerbation by immunoneutralization of lipocortin 1", British J Pharm, 1996, 117, pp. 1145-1154.
Perretti, M., et al., "Annexin A1 and glucocorticoids as effectors of the resolution of inflammation", Nat Rev Immunol, 2009, 1, pp. 62-70.
Purified Mouse Anti-Annexin 1 technical date sheet, BD Transduction Laboratories, 2008.
Rudikoff et al., "Single amino acid substitution altering antigen-binding specificity", Proc Natl Acad Sci USA, 1982, 79(6), pp. 1979-1983.

(56) References Cited

OTHER PUBLICATIONS

Scannell, M., et al., "Annexin-1 and peptide derivatives are released by apoptotic cells and stimulate phagocytosis of apoptotic neutrophils by macrophages", J Immunol, 2007, 178(7), pp. 4595-4605.
Schildbach et al., "Modulation of antibody affinity by a non-contact residue", Protein Sci, 1992, 2, pp. 206-214.
Solito et al., "Annexin A1 in the brain-undiscovered roles?", Trends in Pharmacological Sciences, 2008, 29(3), pp. 135-142.
Sperner-Unterweger, et al., "Schizophrenia and psychoneuroimmunology: an integrative view", Curr Opin Psychiatry, 2015, 28(3), pp. 201-206.
Sun et al., "Annexin-1 is abnormally expressed in Fragile X Syndrome: two-dimensional electrophoresis study in lymphocytes", Am J Med Gene, 2001, 103, pp. 81-90.
Swanborg et al., "Short analytical review, animal models of human disease, experimental autoimmune encephalomyelitis in rodents as a model for human demyelinating disease", Clin Immuno Pathology, 1995, 77, pp. 4-13.
Tagoe et al., "Annexin-1 mediates TNF-alpha-stimulated matrix metalloproteinase secretion from rheumatoid arthritis synovial fibroblasts", J Immunol, 2008, 181(4), pp. 2813-2820.
Tang et al., "Gentic immunization is a simple method for eliciting an immune response", Nature, 1992, 356, pp. 152-154.
Vajdos et al., "Comprehensive functional maps of the antigen-binding site of an anti-ErbB2 antibody obtained with shotgun scanning mutagenesis", J Mol Bioi, 2002, 320(2), pp. 415-428.
van Eden et al., "Immune regulation in adjuvant-induced arthritis, possible implications for innovative therapeutic strategies in arthritis", Arthriris & Rheumatism, 2003, 48(7), pp. 1788-1796.
Vong, L., et al., "Annexin 1 cleavage in activated neutrophils: a pivotal role for proteinase 3", J Biol Chem, 2007, 282(41), pp. 29998-30004.
Walsh et al., "T cells in the central nervous system: messengers of destruction or purveyors of protection?", J Immunol, 2014, 141(3), pp. 340-344.
Wang et al., "Assessing the validity of current mouse genetic models of obsessive-compulsive disorder", Behac Pharm, 2009, 20, pp. 119-133.
Winkler et al., "Changing the antigen binding specificity by single point mutations of an anti-p24 (HIV-1) antibody", J Immuno, 2000, 165(8), pp. 4505-4514.
Xu, G., et al. "Development of High-specificity Antibodies against Renal Urate Transporters Using Genetic Immunization", Journal of Biochemistry and Molecular Biology, 2006, 39(6), pp. 696-702.
Xu. G., et al. "Use of genetic immunization to generate a high-level antibody against rat dicarboxylate transporter", Int Urol Nephrol, 2009, 41, pp. 171-178.
Yang et al., "Anti-inflammatory effect of lipcortin 1 in experimental arthritis", Inflammation 1997, 21(6), pp. 583-596.
Yang et al., "Inhibitory effect of annexin 1 on synovial inflammation in rat adjuvant arthritis", Arthritis Rheum, 1999, 42(7), pp. 1538-1544.
Yang et al., "Modulation of inflammation and response to dexamethasone by Annexin 1 in antigen-induced arthritis", Arthritis Rheum, 2004, 50(3), pp. 976-984.
Yao et al., "Proteomic analysis for anti-atherosclerotic effect of tetrahydroxystilbene glucoside in rats", Biomedicine & Pharmacotherapy, 2013, 67(2), pp. 140-145.
Notice of Allowance dated Mar. 8, 2017 from related U.S. Appl. No. 14/365,311.
Official Action dated Jun. 13, 2017 in related U.S. Appl. No. 14/616,320.
Final Office action dated Jun. 9, 2016 in U.S. Appl. No. 14/365,311.
Office Action dated Dec. 15, 2017 in U.S. Appl. No. 14/365,311.
Office Action dated Jan. 17, 2018 in related U.S. Appl. No. 14/616,320.
NIH Guidelines for Ascites Production in Mice (available online at https://oacu.oir.nih.gov/sites/default/files/uploads/arac-guidelines/ascites.pdf—accessed Mar. 18, 2019).
Milstein's legacy (available online at http://www.whatisbiotechnology.org/index.php/exhibitions/milstein/legacy/The-legacy-of-Milsteins-work—accessed 18 Mar. 2019).
L. R. Jackson et al., "Monoclonal Antibody Production in Murine Ascites, II. Production Characteristics" Laboratory Animal Science, 1999, 49(1):81-86.
L. R. Jackson et al. "Monoclonal Antibody Production in Murine Ascites, I. Clinical and Pathologic Features", Laboratory Animal Science, 1999, 49(1):70-80.
F. M. Hendriksen et al. "Production of monoclonal antibodies by the ascites method in laboratory animals", Research in Immunology, 1998, 149(6):535-542.
W.M. Yokoyama, "Monoclonal Antibody Supernatant and Ascites Fluid Production", 2000, Current Protocols in Immunology, 2.6.1-2.6.9.
B.R. Brodeur and P.S. Tsang, "High yield monoclonal antibody production in ascites", 1986, Journal of Immunological Methods, 86:239-41.
J. Rescher and V. Gerke, "Annexins—unique membrane binding proteins with diverse functions", 2004, Journal of Cell Science, 117:2631-2639.
A. Hofmann et al., "Interactions of Benzodiazepine Derivatives with Annexins", 1998, The Journal of Biological Chemistry, 273(5):2885-2894.
G. Boulougouris et al., IL-2-Independent Activation and Proliferation in Human T Cells Induced by CD28, 1999, J Immunol., 163(4):1809-1816.
C.H. June et al., "Two Distinct Mechanisms of Interleukin-2 Gene Expression in Human T Lymphocytes", 1989, Journal of Autoimmunity, 2 (Supplement), 55-65.
J.D. Dasgupta et al., "The role of class I histocompatibility antigens in the regulation of T-cell activation", 1987, PNAS, 84:1094-1098.
Lerner, "Tapping the immunological repertoire to produce antibodies of predetermined specificity", Nature, 1982, 299, pp. 592-596.
Office Action dated Nov. 13, 2018 in related U.S. Appl. No. 14/365,311.
Office Action dated Nov. 9, 2018 in related U.S. Appl. No. 14/616,320.
Lee, "Effect of disruption of 3D8 complementarity-determining regions on properties of 3D8 antibody", Dissertation submitted to The Graduate School of Ajou University, 2012, pp. 1-71.
Office Action dated Nov. 18, 2019 in related U.S. Appl. No. 14/365,311.
Hay et al., "The Bilag index: a reliable and valid instrument for measuring clinical disease activity in systemic lupus arythematosus", QJM: An International Journal of Medicine, 1993, 86(7), pp. 447-458.
Isenberg et al., "Fifty years of anti-ds DNA antibodies: Are we approaching journey's end?", Rheumatology, 2007, 46(7), pp. 1052-1056.
Iwata et al., "B-cell subsets, signaling and their roles in secretion of autoantibodies" 2016, Lupus, 28(8), pp. 850-856.
Kaplan et al., "Neutrophil Extracellular Traps: Double-Edged Swords of Innate Immunity", The Journal of Immunology, 2012, 189(6), pp. 2689-2695.
Liu et al., "Specific post-translational histone modifications of neutrophil extracellular traps as immunogens and potential targets of lupus autoantibodies", Arthritis Research and Therapy, 2012, 14(R25).
Matsumoto et al., "Interleukin-10-producing plasmablasts exert regulatory function in autoimmune inflammation", Immunity, 2014, 41(6), pp. 1040-1051.
Pepinsky et al., "Monoclonal antibodies to lipocortin-1 as probes for biological function", FEBS Letters 1990, 261(2), pp. 247-252.
Swaak et al., "Predictive value of complement profiles and anti-dsDNA in systemic lupus erythematosus", Annals of the Rheumatic Diseases, 1986, 45, pp. 359-366.
Thieblemont et al., "Human neutrophils in auto-immunity", Seminars in Immunology, 2016, 28(2), pp. 159-173.
Tsokos, "Systemic lupus erythematosus Mechanism of Disease", The New England Journal of Medicine, 2011, 365, pp. 2110.
Cited Document A: "Interleukin 2 (IL-2)", 1990, 79, pp. 1343-1347.
Cited Document B: Matsuzaki et al., "Diseases Caused by Disturbance of Th1/Th2 Balance", 2003, 51(1), pp. 9-13.

(56) References Cited

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Rudikoff et al Single amino acid substitution altering antigen-binding specificity. Proc Natl Acad Sci U S A. Mar. 1982;79(6):1979-83.*
Paul, Fundamental Immunology, 3rd Edition, 1993, pp. 292-295.*
Non-final Office Action dated Jun. 20, 2014 issued in related U.S. Appl. No. 13/131,927.
vanEden et al., "Immune Regulation in Adjuvant-Induced Arthritis, Possible Implications for Innovative Therapeutic Strategies in Arthritis", Arthritis & Rheumatism, 2003, 48(7):1788-1796.
Perretti et al., "Acute inflammatory response in the mouse: exacerbation by immunoneutralization of lipocortin 1", British Journal of Pharmacology, 1996, 117:1145-1154.
Swanborg et al., "Short Analytical Review, Animal Models of Human Disease, Experimental Autoimmune Encephalomyelitis in Rodents as a Model for Human Demyelinating Disease", Clinical Immunology and Pathology, 1995, 77:4-13.
Dijkstra et al., "Multiple sclerosis: some possible therapeutic opportunities", TIPS Reviews, 1993, 14:124-129.
D'Acquisto, F., "From the bench to the pipeline: Testing the immunosuppressive potential of novel therapies targeting annexin A1", Immunology, 2010, 131:159.
D'Acquisto, F., On the adaptive nature of annexin-A 1, Curr Opin Pharmacol. 2009, 9(4):521-8.
D'Acquisto, F., et al., Annexin-1 modulates T-cell activation and differentiation, Blood. 2007, 109 (3):1095-1102.
Notice of Allowance dated Nov. 9, 2014 cited in related U.S. Appl. No. 13/131,927.
Winkler, K. et al. "Changing the Antigen Binding specificity by Single Point Mutations of an Anti-p24 (HIV-1) Antibody", The Journal of Immunology, 2000, 165(8): 4505-4514.
Maynard, J.A. et al., "Protection against anthrax toxin by recombinant antibody fragments correlates with antigen affinity", Nature Biotechnology, 2002, 20(6): 597-601.
O'Kennedy et al., "Antibody Engineering: an overview", Abstract, Essays Biochem, 1991, 26:59-75.

* cited by examiner

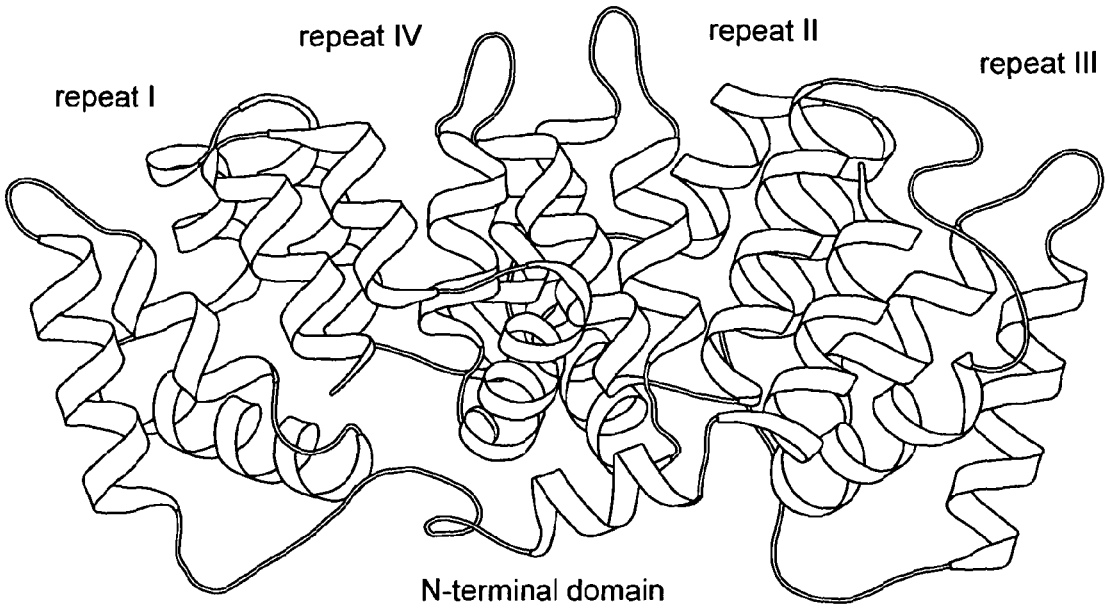
FIG. 1A
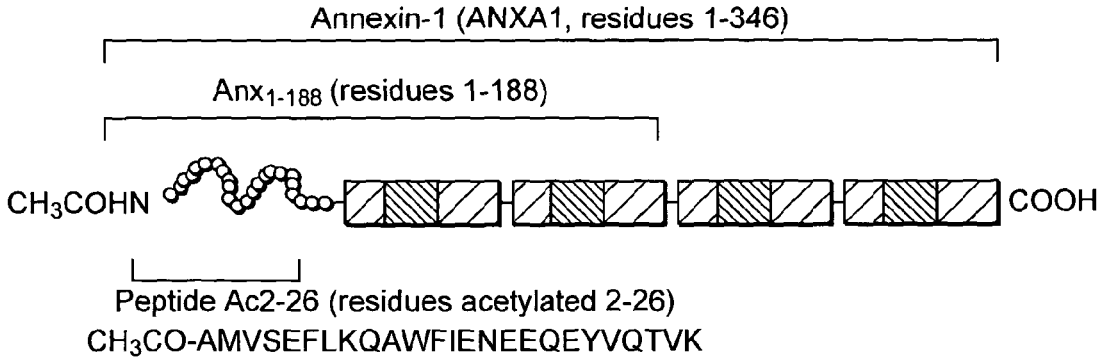
FIG. 1B
$CH_3CO$-AMVSEFLKQAWFIENEEQEYVQTVK
FIG. 1C (i)

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTPAQFDA
121  DELRAAMKGL GTDEDTLIEI LASRTNKEIR DINRVYREEL
161  KRDLAKDITS DTSGDFRNAL LSLAKGDRSE DFGVNEDLAD
201  SDARALYEAG ERRKGTDVNV FNTILTTRSY PQLRRVFQKY
241  TKYSKHDMNK VLDLELKGDI EKCLTAIVKC ATSKPAFFAE
281  KLHQAMKGVG TRHKALIRIM VSRSEIDMND IKAFYQKMYG
321  ISLCQAILDE TKGDYEKILV ALCGGN
```

(ii)

```
1    ATGGCAATGG TATCAGAATT CCTCAAGCAG GCCTGGTTTA
41   TTGAAAATGA AGAGCAGGAA TATGTTCAAA CTGTGAAGTC
81   ATCCAAAGGT GGTCCCGGAT CAGCGGTGAG CCCCTATCCT
121  ACCTTCAATC CATCCTCGGA TGTCGCTGCC TTGCATAAGG
161  CCATAATGGT TAAAGGTGTG GATGAAGCAA CCATCATTGA
201  CATTCTAACT AAGCGAAACA ATGCACAGCG TCAACAGATC
241  AAAGCAGCAT ATCTCCAGGA AACAGGAAAG CCCCTGGATG
281  AAACACTGAA GAAAGCCCTT ACAGGTCACC TTGAGGAGGT
321  TGTTTTGGCT CTGCTAAAAA CTCCAGCGCA ATTTGATGCT
361  GATGAACTTC GTGCTGCCAT GAAGGGCCTT GGAACTGATG
401  AAGATACTCT AATTGAGATT TTGGCATCAA GAACTAACAA
441  AGAAATCAGA GACATTAACA GGGTCTACAG AGAGGAACTG
481  AAGAGAGATC TGGCCAAAGA CATAACCTCA GACACATCTG
521  GAGATTTTCG GAACGCTTTG CTTTCTCTTG CTAAGGGTGA
561  CCGATCTGAG GACTTTGGTG TGAATGAAGA CTTGGCTGAT
601  TCAGATGCCA GGGCCTTGTA TGAAGCAGGA GAAAGGAGAA
641  AGGGGACAGA CGTAAACGTG TTCAATACCA TCCTTACCAC
681  CAGAAGCTAT CCACAACTTC GCAGAGTGTT TCAGAAATAC
721  ACCAAGTACA GTAAGCATGA CATGAACAAA GTTCTGGACC
761  TGGAGTTGAA AGGTGACATT GAGAAATGCC TCACAGCTAT
801  CGTGAAGTGC GCCACAAGCA AACCAGCTTT CTTTGCAGAG
841  AAGCTTCATC AAGCCATGAA AGGTGTTGGA ACTCGCCATA
881  AGGCATTGAT CAGGATTATG GTTTCCCGTT CTGAAATTGA
921  CATGAATGAT ATCAAAGCAT TCTATCAGAA GATGTATGGT
961  ATCTCCCTTT GCCAAGCCAT CCTGGATGAA ACCAAAGGAG
1001 ATTATGAGAA AATCCTGGTG GCTCTTTGTG GAGGAAACTA
1041 A
```

FIG. 2A

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTPAQFDA
121  DELRAAMKGL GTDEDTLIEI LASRTNKEIR DINRVYREEL
161  KRDLAKDITS DTSGDFRNAL LSLAKGDRSE DFGVNEDLAD
201  SDARALYEAG ERRKGTDVNV FNTILTTRSY PQLRRVFQKY
241  TKYSKHDMNK VLDLELKGDI EKCLTAIVKC ATSKPAFFAE
281  KLHQAMKGVG TRHKALIRIM VSRSEIDMND IKAFYQKMYG
321  ISLCQAILDE TKGDYEKILV ALCGGN
```

FIG. 2B

```
1    MNLILRYTFS KMAMVSEFLK QAWFIENEEQ EYVQTVKSSK
41   GGPGSAVSPY PTFNPSSDVA ALHKAIMVKG VDEATIIDIL
81   TKRNNAQRQQ IKAAYLQETG KPLDETLKKA LTGHLEEVVL
121  ALLKTPAQFD ADELRAAMKG LGTDEDTLIE ILASRTNKEI
161  RDINRVYREE LKRDLAKDIT SDTSGDFRNA LLSLAKGDRS
201  EDFG
```

FIG. 2C

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTP
```

FIG. 2D

| Antibody production by genetic immunisation - the direct way from gene to antibody | | |
|---|---|---|
| ✓ | | |
| ✓ | | ► Cloning of the cDNA into a GENOVAC expression vector and confirmation of cell-surface expression |
| | | ► Several intradermal applications of vector DNA absorbed to gold particles |
| | | ► Mouse cells take up the immunisation vector and express the cDNA-encoded foreign protein, stimulating an immune response |
| | | ► Fusion of mouse lymphocytes with murine myeloma cells to produce hybridomas |
| | | ► Specificity testing, cloning of hybridomas, and production of monoclonal antibodies |
| | | |

FIG. 3A

VJ-4B6
Isotype: IgG2b

Legend:
---------- Hybridoma supernatant on cells transfected with pB1-Annexin1
——— Hybridoma supernatant on cells transfected with an irrelevant control cDNA BsaXI BsaXI' BsaXI' BstEII BsaXI BspMI XcmI AACATTGTAATGACCCAATCTCCCAAATCCATGTCCATGTCAGTAGGAGAGAGGGTCACCTTGACCTGCAAGGCCAGTGAGAATGTGGTTACTTATGTTT 100

TTGTAACATTACTGGGTTAGAGGGTTTAGGTACAGGTACAGTCATCCTCTCTCCCAGTGGAACTGGACGTTCCGGTCACTCTTACACCAATGAATACAAA

N I V M T Q S P K S M S M S V G E R V T L T C K A S E N V V T Y V

4B6 VK

CDR1

AgeI SanDI BmrI PvuI BtsI

CCTGGTATCAACAGAAACCAGAGCAGTCTCCTAAACTGCTGATATACGGGGCATCCAACCGGTACACTGGGGTCCCCGATCGCTTCACAGGCAGTGGATC 200

GGACCATAGTTGTCTTTGGTCTCGTCAGAGGATTTGACGACTATATGCCCCGTAGGTTGGCCATGTGACCCCAGGGGCTAGCGAAGTGTCCGTCACCTAG

S W Y Q Q K P E Q S P K L L I Y G A S N R Y T G V P D R F T G S G S

4B6 VK

CDR2

BtsI BbsI BsgI Eco57I

TGCAACAGATTTCACTCTGACCATCAGCAGTGTGCAGGCTGAAGACCTTGCAGATTATCACTGTGGACAGGGTTACAGCTATCCGTACACGTTCGGAGGG 300

ACGTTGTCTAAAGTGAGACTGGTAGTCGTCACACGTCCGACTTCTGGAACGTCTAATAGTGACACCTGTCCCAATGTCGATAGGCATGTGCAAGCCTCCC

A T D F T L T I S S V Q A E D L A D Y H C G Q G Y S Y P Y T F G G

4B6 VK

CDR3

GGGACCAAGCTGGAAATAAAA 321

CCCTGGTTCGACCTTTATTTT

G T K L E I K

4B6 VK

FIG. 11

```
1          10          20 23      30    35    40
NIVMTQSPKSMSMSVGERVTLTCKASENVVTYVSWYQQKP
     Framework 1                CDR1

41         50      57 60          70          80
EQSPKLLIYGASNRYTGVPDRFTGSGSATDFTLTISSVQA
 Framework 2  CDR2          Framework 3

81      88          98       107      115
EDLADYHCGQGYSYPYTFGGGTKLEIKRADAAPTV
             CDR3        J region    C Kappa
```

FIG. 12

```
1          10          20    25    30     36   40
QVQLQQSGPELVRPGTSVKMSCKASGYTFTNYWIGWAKQR
     Framework 1                CDR1

41         5052a       60     66   70          80
PGHGLEWIGDIYPGGDYTNYNEKFKGKATLTADKSSSTAYM
Framework 2          CDR2              Framework 3

8182abc       90   94    100a  103        113
QFSSLTSEDSAIYYCARWGLGYYFDYWGQGITLTVSSAKTTP
                        CDR3      J region      CH1
```

FIG. 14

PvuII PstI Eco57I StuI BciVI

CAGGTCCAGCTGCAGCAGTCTGGACCTGAACTGGTCAGGCCTGGGACTTCAGTGAAGATGTCCTGCAAGGCTTCTGGATACACCTTCACT 90

GTCCAGGTCGACGTCGTCAGACCTGGACTTGACCAGTCCGGACCCTGAAGTCACTTCTACAGGACGTTCCGAAGACCTATGTGGAAGTGA

Q V Q L Q Q S G P E L V R P G T S V K M S C K A S G Y T F T

4B6 VH

CDR1

StuI BpuEI BpmI

AACTACTGGATAGGTTGGGCAAAGCAGAGGCCTGGACATGGCCTTGAGTGGATTGGAGATATTTACCCTGGAGGTGATTATACTAACTAC 180

TTGATGACCTATCCAACCCGTTTCGTCTCCGGACCTGTACCGGAACTCACCTAACCTCTATAAATGGGACCTCCACTAATATGATTGATG

N Y W I G W A K Q R P G H G L E W I G D I Y P G G D Y T N Y

4B6 VH

CDR1 CDR2

BsaXI BpmI PstI BsaXI'

AATGAGAAGTTCAAGGGCAAGGCCACACTGACTGCAGACAAATCCTCCAGCACAGCCTACATGCAGTTCAGCAGCCTGACATCTGAGGAC 270

TTACTCTTCAAGTTCCCGTTCCGGTGTGACTGACGTCTGTTTAGGAGGTCGTGTCGGATGTACGTCAAGTCGTCGGACTGTAGACTCCTG

N E K F K G K A T L T A D K S S S T A Y M Q F S S L T S E D

4B6 VH

CDR2

BciVI BmrI BseRI

TCTGCCATCTATTATTGTGCAAGATGGGGGTTAGGATACTACTTTGACTACTGGGGCCAAGGCATCACTCTCACAGTCTCCTCA 354

AGACGGTAGATAATAACACGTTCTACCCCCAATCCTATGATGAAACTGATGACCCCGGTTCCGTAGTGAGAGTGTCAGAGGAGT

S A I Y Y C A R W G L G Y Y F D Y W G Q G I T L T V S S

4B6 VH

CDR3

*FIG. 13*

ANNEXIN 1 ANTIBODY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue application based on U.S. Pat. No. 9,127,051 which issued on Sep. 8, 2015 from U.S. patent application Ser. No. 13/702,593 filed on Feb. 19, 2013, which is a 35 U.S.C. § 371 national phase application of PCT Application No. PCT/GB2011/000876, filed Jun. 9, 2011, which claims priority to Great Britain Application No. 1011943.6, filed Jul. 15, 2010 and to Great Britain Application No. 1009675.8, filed Jun. 9, 2010, each of which is incorporated herein by reference in its entirety.*

FIELD OF THE INVENTION

The present invention relates to specific binding molecules, particularly antibodies and fragments thereof, which bind to annexin-A1, and hybridoma cell lines which produce such specific binding molecules. Such specific binding molecules are useful in the treatment of T cell-mediated diseases.

BACKGROUND TO THE INVENTION

Glucocorticoids (GCs) are often used for the therapy of a variety of chronic autoimmune diseases because of their ability to simultaneously block both the innate and adaptive immune response. Studies over the last 10 years or so by the present inventors and other research groups have shown that some of the inflammatory effects of GCs on the innate immune response are mediated by a protein called Annexin-1 (Anx-A1). This protein has been proven to exert a homeostatic control over a number of cell types including neutrophils, macrophages and endothelial cells. However, one aspect that has always been neglected is the role of Anx-A1 in the adaptive immune response. This is surprising considering that Anx-A1 has been proposed as one of the second messengers of the pharmacological effects of GCs.

The present inventors have previously shown that Anx-A1 plays a homeostatic role in T cells by modulating the strength of T cell receptor (TCR) signaling (D'Acquisto et al., Blood 109: 1095-1102, 2007).

Furthermore, the inventors have shown that high levels of Anx-A1 lower the threshold of T cell activation and favour the differentiation into Th1 cells, whereas Anx-A1 deficient mice show impaired T cell activation and increased differentiation into Th2 cells (D'Acquisto et al., Eur. J. Immunol. 37: 3131-3142, 2007).

WO 2005/027965 describes the discovery of a mechanism by which apoptotic neutrophils deliver anti-inflammatory signals to dendritic cells and identifies an antibody that interferes with this process.

SUMMARY OF THE INVENTION

The present inventors have identified a monoclonal antibody that has excellent properties in terms of specific inhibition of T cell activation without any adverse cytotoxic effects. The antibody is useful in the treatment of T cell mediated disease, for example rheumatoid arthritis or multiple sclerosis.

Accordingly, the present invention provides a specific binding molecule raised against the human Anx-A1 protein having the amino acid sequence shown in FIG. 2A.

DEFINITIONS

As used herein, a "specific binding molecule" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, receptor-ligand, enzyme-substrate. The present invention is generally concerned with antigen-antibody type reactions. The specific binding molecule of the present invention binds with greater affinity to Anx-A1 than to other molecules, i.e. it binds specifically to Anx-A1. Specific binding molecules which bind to Anx-A1 include anti-Anx-A1 antibodies and aptamers. The specific binding molecule of the present invention is typically an antibody. The anti-Anx-A1 antibodies of the present invention function by blocking the activation of T cells and thus, when administered, can be used in the treatment of T cell-mediated diseases, which are typically caused by aberrant T cell activation.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Antibodies are polypeptides that typically contain two identical heavy chains and two identical light chains, which are smaller than the heavy chains. In mammals there are two types of light chain, which are called lambda (λ) and kappa (κ). Each of the heavy chains and each of the light chains are composed of a variable region and a constant region. The heavy chain variable region is referred to as the $V_H$ region and the light chain variable region is referred to as the $V_L$ region. For kappa light chains, the $V_L$ region can also be referred to as the $V_K$ region. Each of the variable regions of the heavy and light chains comprise three complementarity determining regions (CDRs), CDR1, CDR2 and CDR3. These are named VLCDR1, VLCDR2, VLCDR3, VHCDR1, VHCDR2 and VHCDR3 respectively. Examples of antibodies are the immunoglobulin isotypes (e.g., IgG, IgE, IgM, IgD and IgA) and their isotypic subclasses; fragments which comprise an antigen binding domain such as Fab, $F(ab')_2$, Fv, scFv, dAb, Fd; and diabodies. Antibodies may be polyclonal or monoclonal. A monoclonal antibody may be referred to herein as "mAb".

DETAILED DESCRIPTION OF THE INVENTION

Annexins are a group of calcium- and phospholipid-binding cellular proteins and are also known as lipocortins.

The annexin family has 13 members, including Annexin A1, Annexin A2 and Annexin A5. Annexin-A1 is also known as Annexin-1 and is referred to herein as "Anx-A1". Annexin-1 (Anx-A1) is a 37-kDa protein and was originally described as a mediator of the actions of glucocorticoids. Over the last few years evidence has shown than Anx-A1 plays a homeostatic role in the adaptive immune system, in particular T cells, by modulating the strength of T cell receptor (TCR) signalling. Anx-A1 acts as an endogenous down-regulator of inflammation in cells of the innate immune system in vivo. FIG. 1A is a ribbon diagram showing the three-dimensional structure of Anx-A1.

There are eight human nucleotide sequences which encode Anx-A1. Of these, only four are translated and thus there are four isoforms of Anx-A1, designated ANXA1-002, ANXA1-003, ANXA1-004 and ANXA1-006. These sequences are available from the Ensembl website (www.ensembl.org) and are designated OTTHUMT00000052664 (ANXA1-002), OTTHUMT00000052665 (ANXA1-003), OTTHUMT00000052666 (ANXA1-004) and OTTHUMT00000052668 (ANXA1-006). The amino acid and nucleotide sequences of one isoform of human Annexin-1 (Anx-A1), ANXA1-003, are shown in FIG. 2A. The amino acid sequences of isoforms ANXA1-002, ANXA1-004 and ANXA1-006 are shown in FIGS. 2B, 2C and 2D respectively. As can be seen from FIG. 2, isoforms ANXA1-002, ANXA1-004 and ANXA 1-006 are either short splice variants of ANXA 1-003 or variants of ANXA1-003 with a small number of amino acid changes.

A number of studies have shown that an N-terminal peptide of Anx-A1 named Ac.2-26 acts as a bioactive surrogate of the whole protein (see e.g. Lim et al., Proc Natl Acad Sci USA 95, 14535-9, 1998).

FIG. 1B is a schematic representation of the annexin repeats and the location of this bioactive sequence. Peptide Ac.2-26 is an acetylated peptide having the sequence of amino acid residues 2-26 of the full-length amino acid sequence of Anx-A1 shown in FIG. 2. The sequence of peptide Ac.2-26 is shown in FIG. 1C and is as follows:

$CH_3CO$-AMVSEFLKQAWFIENEEQEYVQTVK (SEQ ID NO: 1)

Anx-A1 and its N-terminal derived bioactive peptides mediate their biological effects through members of the formyl peptide receptor (FPR) family. Anx-A1 exerts its counterregulatory actions on neutrophil extravasation and innate immunity by direct binding and activation of one member of this family, formyl peptide receptor like-1 (FPRL-1). The present inventors have previously found that stimulation of T cells in the presence of hrAnx-A1 increases T cell activation via stimulation of FPRL-1 (D'Acquisto et al., Blood 109: 1095-1102, 2007).

The specific binding molecule of the present invention binds to Annexin-1 (Anx-A1). The Anx-A1 to which the specific binding molecule binds is human Anx-A1 having the polypeptide sequence shown in FIG. 2A.

In a first aspect, the present invention provides a specific binding molecule raised against the human Anx-A1 protein having the amino acid sequence shown in FIG. 2A.

This aspect of the invention also extends to a specific binding molecule comprising the Complementarity Determining Regions (CDRs) VLCDR1, VLCDR2, VLCDR3, VHCDR1, VHCDR2 and VHCDR3 of the specific binding molecule of the first aspect of the invention or an amino acid sequence at least 70% identical to each of the respective CDRs. The specific binding molecule is typically an antibody.

In one embodiment, the specific binding molecule comprises Complementarity Determining Regions (CDRs) [VLCDR1, VLCDR2, VLCDR3,] VHCDR1, VHCDR2 and VHCDR3, each having a respective amino acid sequence as follows in which

| | |
|---|---|
| [VLCDR1 is KASENVVTYVS | (SEQ ID NO:2) |
| VLCDR2 is GASNRYT | (SEQ ID NO:3) |
| VLCDR3 is GQGYSYPYT | (SEQ ID NO:4)] |
| VHCDR1 is GYTFTNYWIG | (SEQ ID NO:5) |
| VHCDR2 is DIYPGGDYTNYNEKFKG | (SEQ ID NO:6) |
| VHCDR3 is WGLGYYFDY | (SEQ ID NO:7) |

or an amino acid sequence at least 70% identical thereto.

The CDRs are designated according to a combination of conserved sequence definition (Kabat et al in "Sequences of Proteins of Immunological Interest", Nat'l. Inst. Health, Bethesda, Md. (1987)), and structural definition (Chothia and Lesk J. Mol Biol. 196:901-17(1987)). These definitions were also subsequently described in Carter et al, Proc Nat'l Acad Sci USA. 89:4285-9 (1992).

The present invention also extends to variants of peptide sequences referred to above. As used herein the term "variant" relates to proteins which have a similar amino acid sequence and/or which retain the same function. For instance, the term "variant" encompasses proteins or polypeptides which include one or more amino acid additions, deletions, substitutions or the like. An example of a variant of the present invention is a protein, such as a fusion protein, comprising a peptide as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions. The present invention therefore extends to a specific binding molecule comprising CDRs having the amino acid sequences described above but with one or more conservative substitutions in the CDRs, such that the amino acid sequences of the CFRs have at least 70% identity to those described above. For example, each CDR may have 1, 2, 3, 4 or 5 conservative substitutions (depending on the CDR) compared to the amino acid sequences of the CDRs set out above. For example, there can be 1, 2 or 3 conservative substitutions in the amino acid sequence of VLCDR1 set out above, 1 or 2 conservative substitutions in the amino acid sequence of VLCDR2 set out above, 1 or 2 conservative substitutions in the amino acid sequence of VLCDR3 set out above, 1, 2 or 3 conservative substitutions in the amino acid sequence of VHCDR1 set out above, 1, 2, 3, 4 or 5 conservative substitutions in the amino acid sequence of VHCDR2 set out above and 1, 2 or 3 conservative substitutions in the amino acid sequence of VHCDR3 set out above, and the sequence will still retain at least 70% identity to the CDR sequences set out above.

Using the three letter and one letter codes the amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the protein, such as a fusion protein, referred to above. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This can be done to alter the properties of a substance of the present invention (e.g. to assist in identification, purification or expression, as explained above in relation to fusion proteins).

Amino acid changes relative to the sequence given above can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Typically, the amino acid sequence of the CDRs of the specific binding molecule of the invention have at least 70% identity, using the default parameters of the BLAST computer program (Atschul et al., J. Mol. Biol. 215, 403-410 (1990)) provided by HGMP (Human Genome Mapping Project), at the amino acid level, to the amino acid sequences of the CDRs described above. More typically, the CDR sequence has at least 75%, 80%, 85%, 90%, 91%, 92%, 93%, 94%, 95%, 96%, 97%, 98% or at least 99% identity, at the amino acid level, to the sequences shown above. Typically, each of the CDR sequences of the specific binding molecule of the invention has this level of identity to the amino acid sequences of the CDRs set out above. Alternatively, any 1, 2, 3 4 or 5 of the CDRs of the specific binding molecule of the invention has this level of identity to the amino acid sequences of the CDRs set out above.

The specific binding molecule of the invention is typically an antibody, more typically a monoclonal antibody. In one embodiment, the monoclonal antibody of the present invention is humanised.

The monoclonal antibody of the present invention can be humanised by modifying the amino acid sequence of the antibody. Methods to reduce the immunogenicity of the specific binding molecules of the invention include CDR grafting on to a suitable antibody framework scaffold or variable surface residues remodelling, e.g. by site-directed mutagenesis or other commonly used molecular biological techniques (Roguska et al Protein Eng. 9 895-904 (1996)).

Other methods applicable can include the identification of potential T-cell epitopes within the molecule, and the subsequent removal of these e.g. by site-directed mutagenesis (de-immunisation). Humanisation of the specific binding molecule may be desired where the molecule is to be used as a therapeutic agent. Humanisation of the CDR regions or of the surrounding framework sequence can be carried out as desired.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539

The specific binding molecule of the invention can be a fragment of an antibody. It has been shown that fragments of a whole antibody can perform the function of binding antigens. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment (Ward, E. S. et al., Nature 341:544-546 (1989)) which consists of a $V_H$ domain; (v) isolated CDR regions; (vi) $F(ab')_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl Acad. Sci. USA 90: 6444-6448 (1993)). Typically, the fragment is a Fab, $F(ab')_2$ or Fv fragment or an scFv molecule.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnot 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Monoclonal antibody VJ-4B6 is secreted by the hybridoma cell line VJ-4B6-E5-B10-D4 deposited on 3 Jun. 2010 with the European Collection of Cell Cultures (ECACC), Health Protection Agency, Centre for Emergency Preparedness and Response, Porton Down, Salisbury, SP4 0JG, United Kingdom, under the Budapest Treaty, and designated by the accession no. 10060301.

The deposit was made by Fulvio D'Acquisto, Queen Mary and Westfield College, Centre for Biochemical Pharmacology, Charterhouse Square, London EC1M 6BQ.

The depositor has authorised the applicant to refer to the deposited material in the application and has given his unreserved and irrevocable consent to the deposited material being made available to the public in accordance with Rule 31(1)(d) of the European Patent Convention.

The hybridoma cell line VJ-4B6-E5-B10-D4 produces the monoclonal antibody VJ-4B6 that specifically binds to Annexin-A1. The monoclonal antibody VJ-4B6 of the present invention is of the IgG2b isotype.

The antibody VJ-4B6 was raised against the full-length human Anx-A1 protein having the amino acid sequence shown in FIG. 2A.

The DNA and amino acid sequence of the light chain variable region of the antibody VJ-4B6 are shown in FIG. 11. FIG. 12 shows the amino acid sequence of the light chain variable region of VJ-4B6 with the CDRs annotated. FIG. 12 also shows the first few amino acids of the light chain constant region of VJ-4B6.

The DNA and amino acid sequence of the heavy chain variable region of the antibody VJ-4B6 are shown in FIG. 13. FIG. 14 shows the amino acid sequence of the heavy chain variable region of VJ-4B6 with the CDRs annotated. FIG. 14 also shows the first few amino acids of the heavy chain constant region of VJ-4B6.

The CDRs of the antibody VJ-4B6 are as follows:

| | |
|---|---|
| [VLCDR1 is KASENVVTYVS | (SEQ ID NO:2) |
| VLCDR2 is GASNRYT | (SEQ ID NO:3) |
| VLCDR3 is GQGYSYPYT | (SEQ ID NO:4)] |
| VHCDR1 is GYTFTNYWIG | (SEQ ID NO:5) |
| VHCDR2 is DIYPGGDYTNYNEKFKG | (SEQ ID NO:6) |
| VHCDR3 is WGLGYYFDY | (SEQ ID NO:7) |

The present invention extends to specific binding molecules having the CDRs of the antibody VJ-4B6, as described herein, and also to specific binding molecules having CDRs with at least 70% identity to one or more of the CDRs of the antibody VJ-4B6, as described herein.

The present invention also extends to specific binding molecules having either the light chain variable region, the heavy chain variable region or both the light chain variable region and the heavy chain variable region of the antibody VJ-4B6.

In a specific embodiment, the present invention therefore provides a specific binding molecule in accordance with the first aspect of the invention comprising a polypeptide having an amino acid sequence as shown in FIG. 11 and/or FIG. 13.

This embodiment of the invention also extends to certain antibody fragments which contain the light chain variable region having the amino acid sequence shown in FIG. 11 and/or the heavy chain variable region having the amino acid sequence shown in FIG. 13. For example, this embodiment extends to Fab, $F(ab')_2$ or Fv fragments and scFv molecules.

The present invention also encompasses specific binding molecules in accordance with the first aspect of the invention comprising a polypeptide having an amino acid sequence as shown in FIG. 12 and/or FIG. 14.

In a specific embodiment, the present invention provides a specific binding molecule in accordance with the first aspect of the invention produced by the hybridoma cell line deposited with the European Collection of Cell Cultures (ECACC) on 3 Jun. 2010 as Accession No. 10060301.

In a second aspect, the present invention provides a hybridoma cell line which produces a specific binding molecule raised against the human Anx-A1 protein having the amino acid sequence shown in FIG. 2A.

In a specific embodiment, the present invention provides a hybridoma cell line in accordance with the second aspect of the invention deposited with the European Collection of Cell Cultures (ECACC) on 3 Jun. 2010 as Accession No. 10060301.

In a third aspect, the present invention provides a pharmaceutical composition comprising a specific binding molecule of the invention.

The composition in accordance with this aspect of the invention can be formulated for use by any convenient route. The pharmaceutical composition of the invention will normally include a pharmaceutically acceptable carrier, excipient, diluent, adjuvant, vehicle, buffer or stabiliser in addition to a specific binding molecule of the invention. Such carriers include, but are not limited to, saline, buffered saline, dextrose, liposomes, water, glycerol, polyethylene glycol, ethanol and combinations thereof. This pharmaceutical composition may be in any suitable form depending upon the desired method of administering it to a patient.

It can be provided in unit dosage form, will generally be provided in a sealed container and may be provided as part of a kit. Such a kit would normally (although not necessarily) include instructions for use. It can include a plurality of said unit dosage forms.

The pharmaceutical composition can be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions can be prepared by any method known in the art of pharmacy, for example by admixing the active ingredient with the carrier(s) or excipient(s) under sterile conditions.

Pharmaceutical compositions adapted for oral administration can be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which can be used include for example water, polyols and sugars. For the preparation of suspensions, oils (e.g. vegetable oils) can be used to provide oil-in-water or water in oil suspensions.

Pharmaceutical compositions adapted for transdermal administration can be presented as discrete patches intended to remain in intimate contact with the epidermis of the recipient for a prolonged period of time. For example, the active ingredient can be delivered from the patch by iontophoresis as generally described in Pharmaceutical Research, 3(6):318 (1986).

Pharmaceutical compositions adapted for topical administration can be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient can be employed with either a paraffinic or a water-miscible ointment base. Alternatively, the active ingredient can be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration can be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists that can be generated by means of various types of metered dose pressurised aerosols, nebulizers or insufflators.

Pharmaceutical compositions adapted for vaginal administration can be presented as pessaries, tampons, creams, gels, pastes, foams or spray formulations.

Pharmaceutical compositions adapted for parenteral administration include aqueous and non-aqueous sterile injection solution which can contain anti-oxidants, buffers, bacteriostats and solutes which render the formulation substantially isotonic with the blood of the intended recipient; and aqueous and non-aqueous sterile suspensions which can include suspending agents and thickening agents. Excipients which can be used for injectable solutions include water, alcohols, polyols, glycerine and vegetable oils, for example. The compositions can be presented in unit-dose or multi-dose containers, for example sealed ampoules and vials, and can be stored in a freeze-dried (lyophilized) condition requiring only the addition of the sterile liquid carried, for example water for injections, immediately prior to use. Extemporaneous injection solutions and suspensions can be prepared from sterile powders, granules and tablets.

The pharmaceutical compositions can contain preserving agents, solubilising agents, stabilising agents, wetting agents, emulsifiers, sweeteners, colourants, odourants, salts (substances of the present invention can themselves be provided in the form of a pharmaceutically acceptable salt), buffers, coating agents or antioxidants.

The pharmaceutical compositions of the invention can also contain one or more other therapeutically active agents in addition to the molecule of the present invention.

In some embodiments, the formulation of the active drug concentrate can comprise a pharmaceutically acceptable tonicity agent, a buffering agent, and a pharmaceutically acceptable surfactant.

Alternatively, the formulation can comprise the active ingredient plus sodium phosphate, monobasic, sodium phosphate dibasic, sodium chloride, polysorbate 80 or polysorbate 20 (surfactant to minimise risk of agitation-induced aggregation) and water (USP/Ph.Eur), optionally with a pH adjusted to about 6.0 to 7.0, e.g. around 6.5.

The active drug concentrate may or may not be lyophilised.

Other formulations can comprise sodium acetate trihydrate as a buffering agent, sodium chloride as a tonicity modifier, acetic acid for pH adjustment, and water for injection.

Dosages of the composition of the present invention can vary between wide limits, depending upon the disease or disorder to be treated, the age and condition of the individual to be treated, etc. and a physician will ultimately determine appropriate dosages to be used.

This dosage can be repeated as often as appropriate. If side effects develop the amount and/or frequency of the dosage can be reduced, in accordance with normal clinical practice.

For administration to mammals, and particularly humans, it is expected that the daily dosage of the active agent will be from 1 μg/kg to 10 mg/kg body weight, typically around 10 μg/kg to 1 mg/kg body weight. The physician in any event will determine the actual dosage which will be most suitable for an individual which will be dependent on factors including the age, weight, sex and response of the individual.

The above dosages are exemplary of the average case. There can, of course, be instances where higher or lower dosages are merited, and such are within the scope of this invention.

The specific binding molecules of the invention can be used in medicine, for example in the treatment of T cell-mediated diseases.

In a fourth aspect, the present invention therefore provides a specific binding molecule of the invention for use in medicine.

In a fifth aspect, the present invention provides a specific binding molecule of the invention for use in the treatment of a T cell-mediated disease. This aspect of the invention therefore also includes a method for the treatment of a T cell-mediated disease in a subject, typically a subject in need thereof, comprising administering to the subject a specific binding molecule of the invention. The invention therefore also extends to the use of a specific binding molecule of the invention in the manufacture of a medicament for use in the treatment of a T cell-mediated disease or alternatively to the use of a specific binding molecule of the invention in the manufacture of a medicament for the treatment of a T cell-mediated disease. The method of treatment can be of a human or an animal subject and the invention extends equally to uses in both human and/or veterinary medicine. The specific binding molecule of the invention is preferably administered to an individual in a "therapeutically effective amount", this being sufficient to show benefit to the individual. As used herein, "treatment" includes any regime that can benefit a human or non-human animal, preferably mammal. The treatment may be in respect of an existing condition or may be prophylactic (preventative treatment).

In this aspect of the invention, the specific binding molecule of the invention can be used to treat a wide range of diseases which are mediated by T cells. In the present context, "T cell-mediated disease" means any disease or condition in which T cells play a role in pathogenesis or development of the disease or condition. T cell-mediated diseases are typically caused by aberrant T cell activation. Accordingly, such diseases can be treated by preventing the activation of T cells by blocking the activity of Anx-A1, which as demonstrated herein can be effected by the monoclonal antibody VJ-4B6. Typically, the T cell-mediated diseases treated in the present invention are diseases in which Th1 cells play a role.

T cell-mediated diseases include but are not limited to graft-versus-host disease, graft rejection, atherosclerosis, HIV and/or AIDS, psoriasis, miscarriage, and some autoimmune diseases. Autoimmune diseases which can be treated according to the present invention include rheumatoid arthritis (RA), multiple sclerosis (MS), systemic lupus erythematosus (SLE), Addison's disease, Grave's disease, scleroderma, polymyositis, diabetes and in particular some forms of diabetes mellitus (for example juvenile onset diabetes), autoimmune uveoretinitis, ulcerative colitis, pemphigus vulgaris, inflammatory bowel disease, autoimmune thyroiditis, uveitis, Behcet's disease and Sjögren's syndrome. The T cell-mediated disease is typically rheumatoid arthritis, multiple sclerosis, systemic lupus erythematosus, atherosclerosis, HIV, AIDS or psoriasis. More typically, the T cell-mediated disease is rheumatoid arthritis or multiple sclerosis, T cell-mediated diseases as defined herein also include miscarriage. As defined herein, treatment may be prophylactic (preventative treatment). The specific binding molecule of the invention can thus be used to prevent miscarriage. An uncontrolled Th1 response is known to be implicated in miscarriage, and increasing a Th2 response favours pregnancy.

The T cell-mediated disease is typically rheumatoid arthritis. In rheumatoid arthritis (RA), it is thought that T cells recognise and interact with antigen presenting cells in the synovium. Once activated, these cells produce cytokines and effector molecules; this sequential, expanded production of cytokines constitutes the "cytokine cascade" that results in the activation of macrophages and induction of the inflammatory process, culminating in degradation and resorption of cartilage and bone. Over time, bone erosion, destruction of cartilage, and complete loss of joint integrity can occur. Eventually, multiple organ systems may be affected.

In another embodiment, the T cell-mediated disease is multiple sclerosis (MS).

In another embodiment, the T cell-mediated disease is atherosclerosis. Inflammation plays a key role in coronary artery disease and other manifestations of atherosclerosis. Immune cells dominate early atherosclerotic lesions, their effector molecules accelerate progression of the lesions, and activation of inflammation can elicit acute coronary syndromes. Adaptive immunity is highly involved in atherogenesis since it has been shown to interact with metabolic risk factors to initiate, propagate, and activate lesions in the arterial tree.

In another embodiment, the T cell-mediated disease is systemic lupus erythematosus (SLE).

In relation to the ability of Anx-A1 to favour differentiation of Th1 cells, the present invention can also be used, for example, to limit uncontrolled protective cellular (Th1) responses against intracellular pathogens and to treat extracellular infection (Th2 response) by suppressing Th1 differentiation and favouring Th2 differentiation.

Preferred features for the second and subsequent aspects of the invention are as for the first aspect mutatis mutandis.

In one embodiment, the present invention provides a specific binding molecule raised against the full-length human Anx-A1 protein having the amino acid sequence shown in FIG. 2A.

One example of such a specific binding molecule is the monoclonal antibody VJ-4B6 produced by the hybridoma cell line deposited with the European Collection of Cell Cultures (ECACC) on 3 Jun. 2010 as Accession No. 10060301.

In one embodiment, the present invention provides a specific binding molecule having the CDRs of the monoclonal antibody VJ-4B6, which have the following amino acid sequences:

| | |
|---|---|
| [VLCDR1 is KASENVVTYVS | (SEQ ID NO:2) |
| VLCDR2 is GASNRYT | (SEQ ID NO:3) |
| VLCDR3 is GQGYSYPYT | (SEQ ID NO:4)] |
| VHCDR1 is GYTFTNYWIG | (SEQ ID NO:5) |
| VHCDR2 is DIYPGGDYTNYNEKFKG | (SEQ ID NO:6) |
| VHCDR3 is WGLGYYFDY | (SEQ ID NO:7) |

In one embodiment, the present invention provides a specific binding molecule having the $V_H$ and/or $V_L$ regions of the monoclonal antibody VJ-4B6, which are shown in FIGS. 11 and 13 respectively.

In one embodiment, the present invention provides the hybridoma cell line VJ-4B6-E5-B10-D4 deposited with the European Collection of Cell Cultures (ECACC) on 3 Jun. 2010 as Accession No. 10060301.

The monoclonal antibody VJ-4B6 was produced by a method described in FIG. 3A. Briefly, cDNA encoding full-length human Anx-A1 having the sequence shown in FIG. 2A was cloned into an expression vector and cell-surface expression confirmed. Several intradermal applications of vector DNA adsorbed to gold particles were then administered to mice. The mouse cells took up the immunization vector and expressed the cDNA-encoded protein, stimulating an immune response. Mouse lymphocytes were then fused with murine myeloma cells to produce hybridomas. Specificity testing was then carried out, the hybridomas cloned and the monoclonal antibody produced.

The approach used to produce the monoclonal antibody VJ-4B6 thus uses Anx-A1 cDNA-transfected cells which express the whole molecule on the cell surface and hence the protein is in the same form as would be found in vivo, i.e. in its quaternary native structure. This approach for the production of antibodies differs from the production of other commercially-available antibodies to Anx-A1, which have been generated by immunizing mice with Anx-A1 peptide or denatured full-length protein.

The antibody of the invention is particularly useful in the treatment of T cell-mediated diseases such as rheumatoid arthritis and multiple sclerosis.

The present invention will now be further described by way of reference to the following Examples which are present for the purposes of illustration only. In the Examples, reference is made to a number of Figures in which:

FIG. 1A is a ribbon diagram of annexin-1 structure showing the four annexin repeats and the N-terminal domain. FIG. 1B is a schematic representation of the annexin repeats and the location of the bioactive sequence, Annexin-1 peptide Ac,2-26. FIG. 1C shows the amino acid sequence of peptide Ac.2-26, which is an acetylated N-terminal peptide fragment of Anx-A1.

FIG. 2A shows (i) the amino acid sequence (SEQ ID NO:8) and (ii) the nucleotide sequence (SEQ ID NO:9) of human Annexin-1 (Anx-A1), isoform ANXA1-003. FIG. 2B shows the amino acid sequence of human Annexin-1 (Anx-A1), isoform ANXA1-002 (SEQ ID NO:10). FIG. 2C shows the amino acid sequence of human Annexin-1 (Anx-A1), isoform ANXA1-004 (SEQ ID NO:11). FIG. 2D shows the amino acid sequence of human Annexin-1 (Anx-A1), isoform ANXA1-006 (SEQ ID NO:12).

FIG. 3 shows the generation of VJ-4B6. (A) Schematic representation of the strategy used to isolate and produce VJ-4B6. (B) The histogram shows the staining of cell lines stably transfected with Annexin-1 cDNA (green line; right-hand peak) or an irrelevant control cDNA (red line; left-hand peak) with VJ-4B6.

FIG. 4 shows validation of VJ-4B6. (A) Staining of permeabilised human Peripheral Blood Mononuclear Cells (PBMC) or Polymorph Mononuclear Cells (PMN) with VJ-4B6 (50 ng/ml). (B) Staining of permeabilized murine splenocytes or resident peritoneal macrophages with VJ-4B6 (50 ng/ml). In all tests, cells were fixed with 4% paraformaldehyde and then permeabilised with 0.02% saponin in FACS buffer. Cells were incubated with biotinylated VJ-4B6 overnight at 4° C. and then stained for 1 hour using a streptavidin-FITC conjugated antibody (dil. 1:200). In all graphs, left-hand peak represents control and right-hand peak represents VJ-4B6. The data shown are from a single experiment and are representative of other two experiments with similar results.

FIG. 5 shows that VJ-4B6 inhibits anti-CD3-induced T cell proliferation. T cells from spleen and lymph nodes of AnxA1+/+ (A) and AnxA1−/− (B) mice were stimulated with plate-bound anti-CD3(1 μg/ml) in presence of the indicated concentrations of VJ-4B6. After 18-20 hours, cells were pulsed with 3H-thymidine (1 μCi) for 12 hours and then processed by cell-harvester to measure the levels of 3H-thymidine incorporation. The data shown are from a single experiment and are representative of other two experiments with similar results.

FIG. 6 shows that VJ-4B6 inhibits anti-CD3/CD28-induced T cell proliferation. T cells from spleen and lymph nodes of AnxA1+/+ (A) and AnxA1−/− (B) mice were stimulated with plate-bound anti-CD3(1 μg/ml) and anti-CD28 (1 μg/ml) in presence of the indicated concentrations of VJ-4B6. After 18-20 hours, cells were pulsed with 3H-thymidine (1 μCi) for 12 hours and then processed by cell-harvester to measure the levels of 3H-thymidine incorporation. The data shown are from a single experiment and are representative of other two experiments with similar results.

Figure 7A:
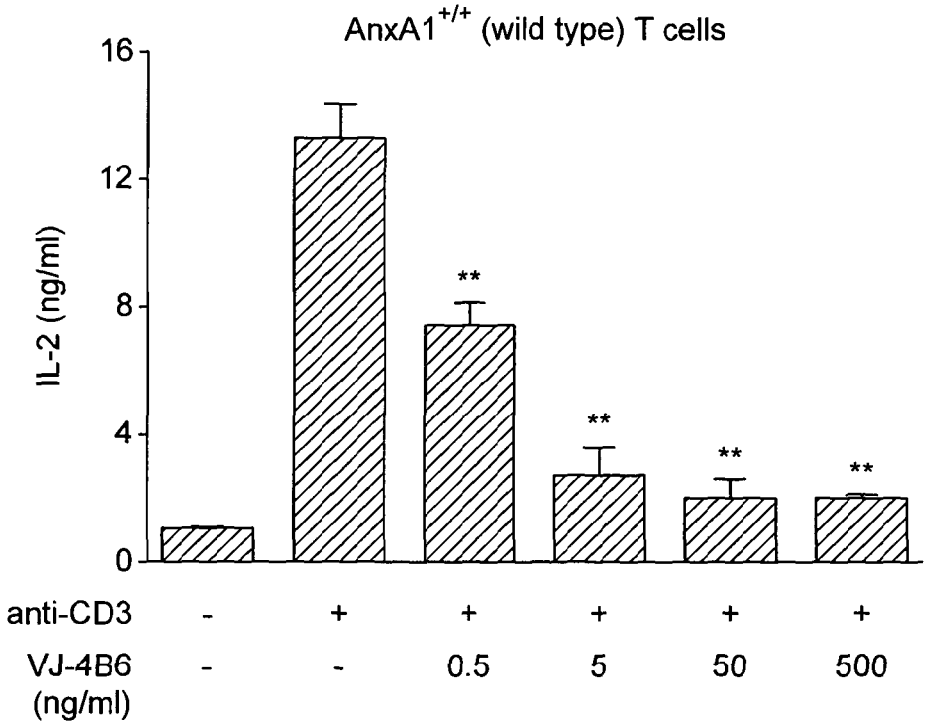
Figure 7B:
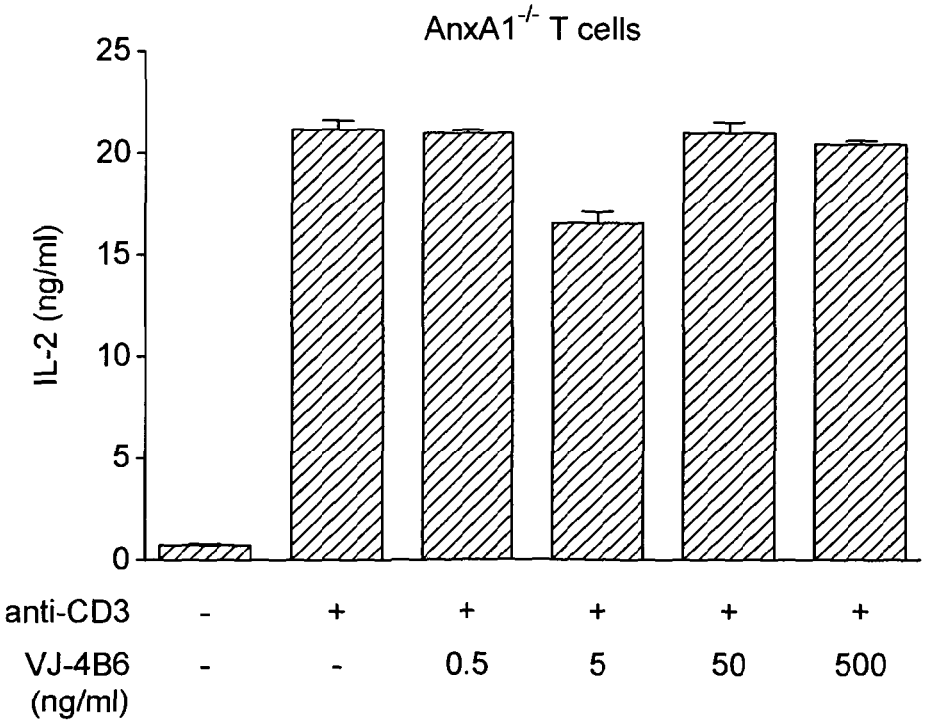

FIG. 7 shows that VJ-4B6 inhibits anti-CD3-induced IL-2 production. T cells from spleen and lymph nodes of AnxA1+/+ (A) and AnxA1−/− (B) mice were stimulated with plate-bound anti-CD3 (1 μg/ml) in presence of the indicated concentrations of VJ-4B6. After 20-24 hours, cell supernatants were collected and analyzed for the levels of IL-2 by ELISA. The data shown are from a single experiment and are representative of other two experiments with similar results.

Figure 8A:
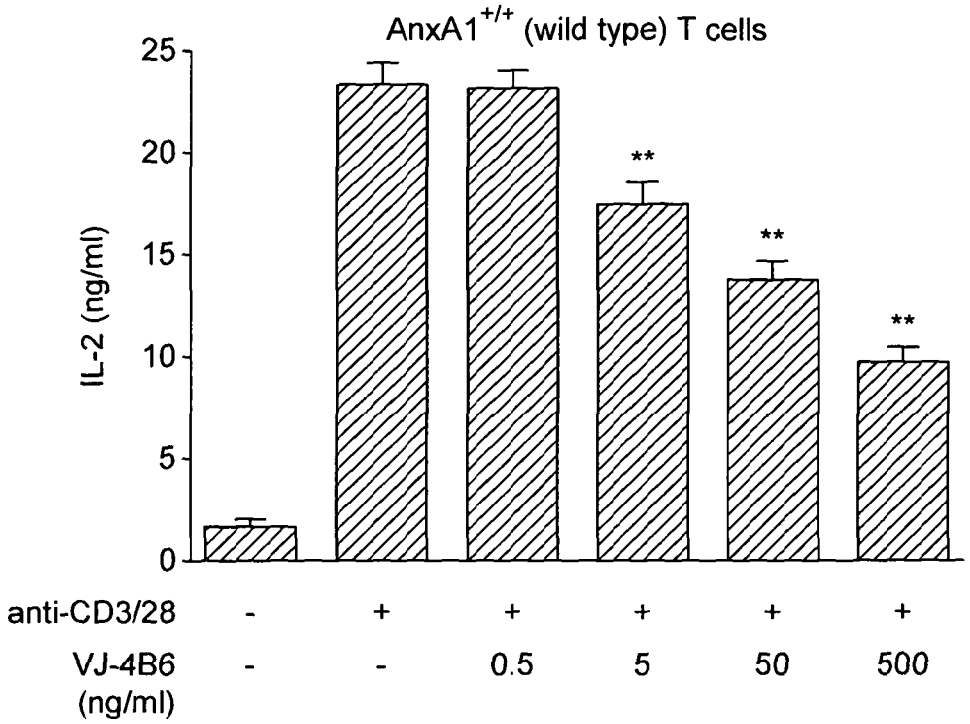
Figure 8B:
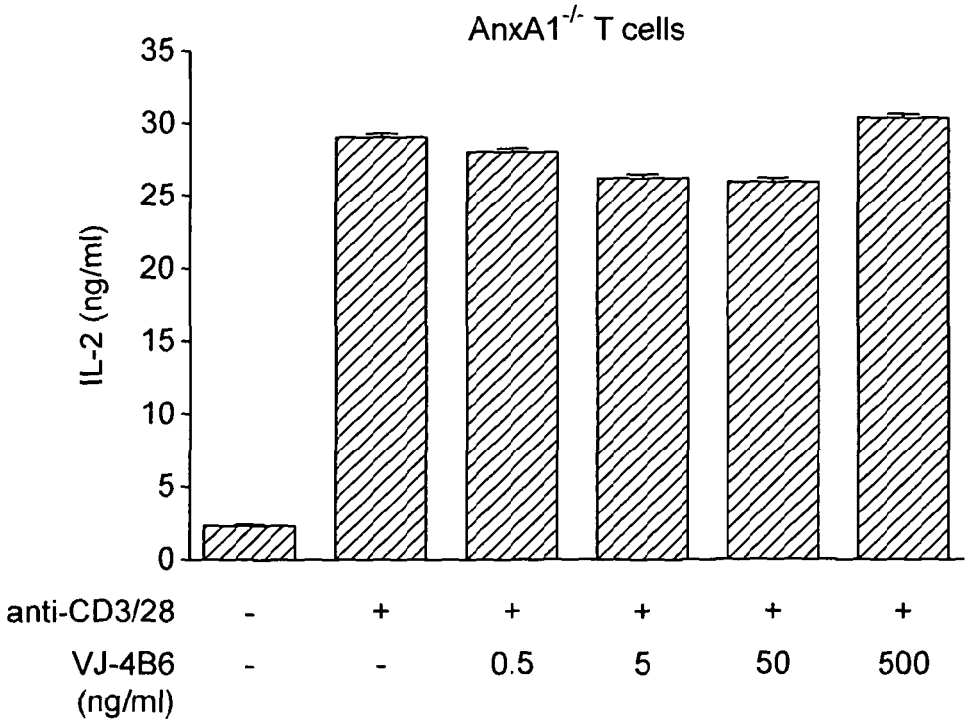

FIG. 8 shows that VJ-4B6 inhibits anti-CD3/CD28-induced IL-2 production. T cells from spleen and lymph nodes of AnxA1+/+ (A) and AnxA1−/− (B) mice were stimulated with plate-bound anti-CD3 (1 μg/ml) and anti-CD28 (1 μg/ml) in presence of the indicated concentrations of VJ-4B6. After 20-24 hours, cell supernatants were collected and analyzed for the levels of IL-2 by ELISA. The data shown are from a single experiment and are representative of other two experiments with similar results.

Figure 9A:
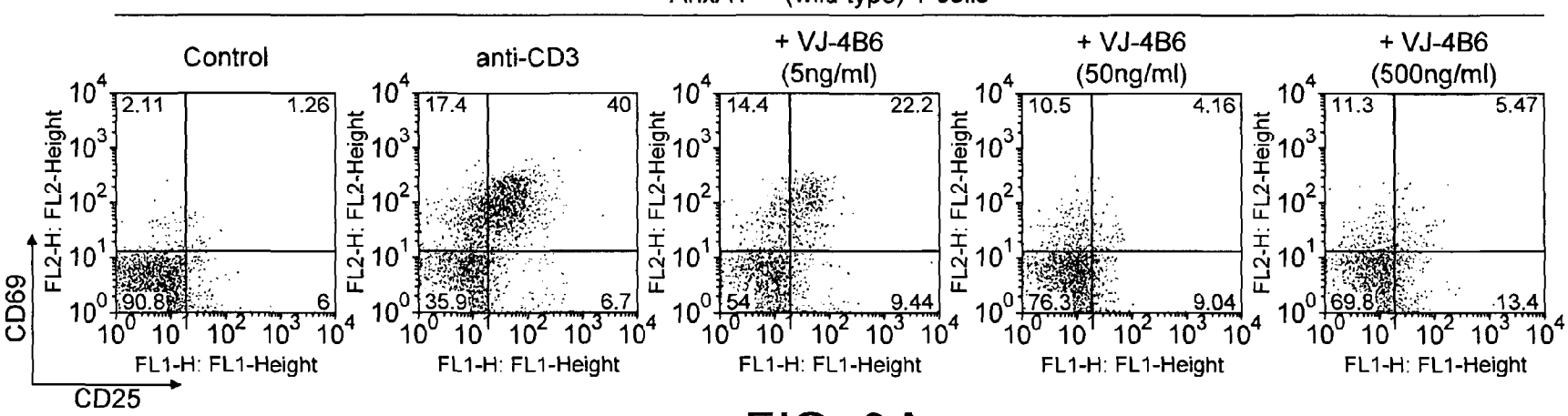
Figure 9B:
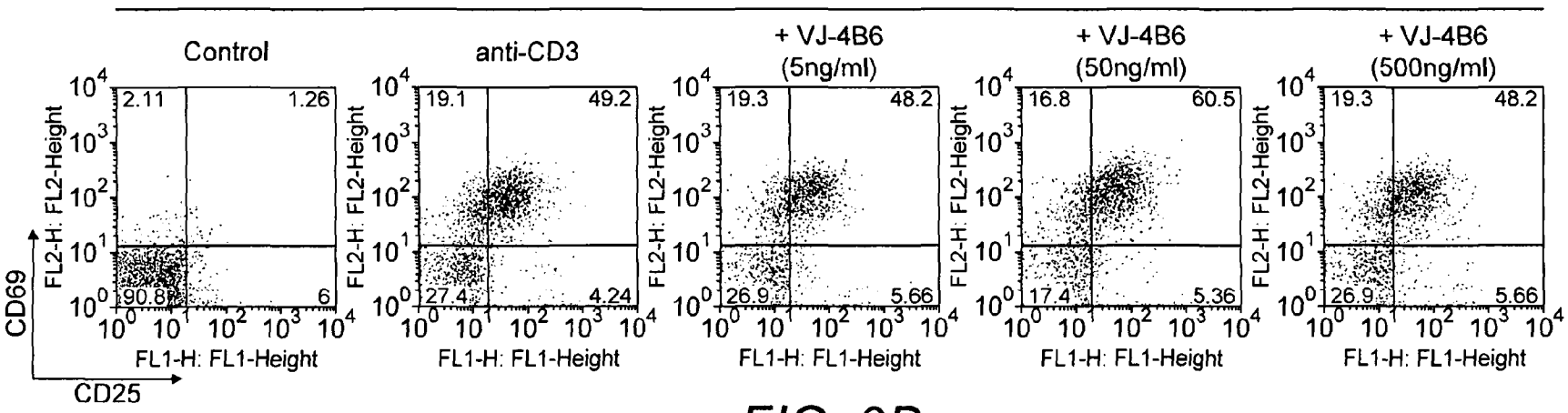

FIG. 9 shows that VJ-4B6 inhibits anti-CD3-induced CD25/CD69 upregulation. T cells from spleen and lymph nodes of AnxA1+/+ (A) and AnxA1−/− (B) mice were stimulated with plate-bound anti-CD3 (1 μg/ml) in presence of the indicated concentrations of VJ-4B6. After 18-20 hours, cells were collected and stained with anti-CD25 FITC plus anti-CD69 PE. Samples were acquired by FACScalibur and analyzed by FlowJo software. The data shown are from a single experiment and are representative of other two experiments with similar results.

Figure 10A:
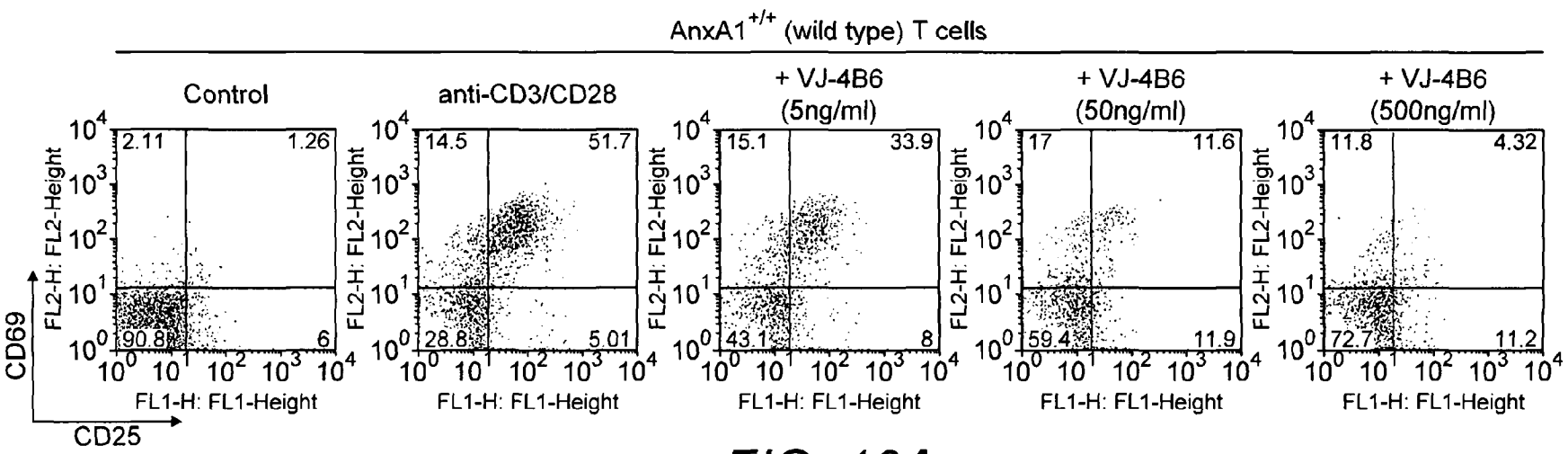
Figure 10B:
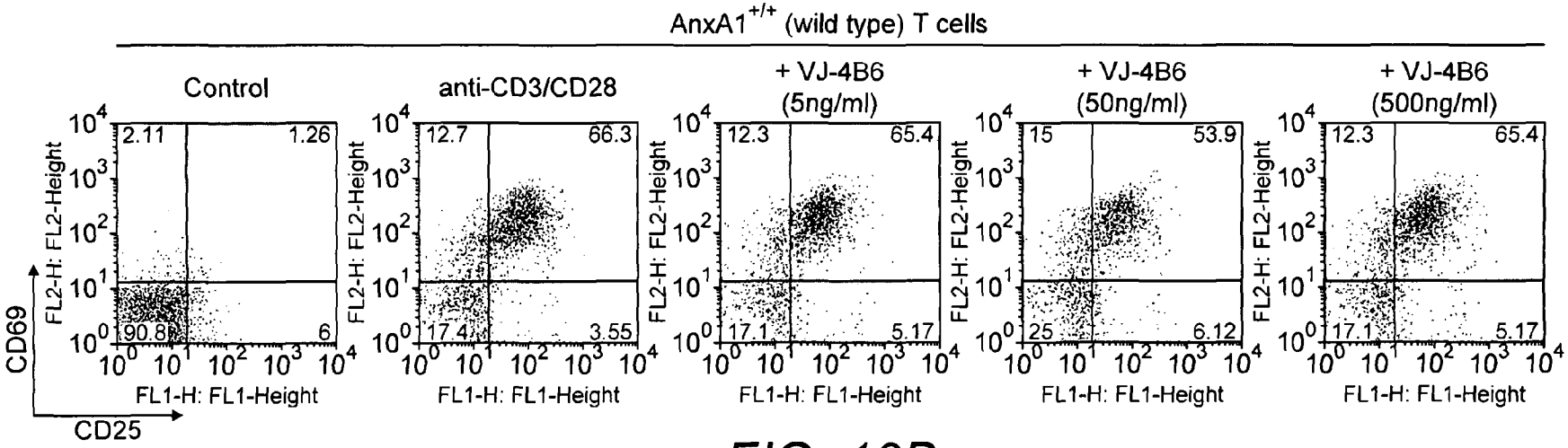

FIG. 10 shows that VJ-4136 inhibits anti-CD3/CD28-induced CD25/CD69 upregulation. T cells from spleen and lymph nodes of AnxA1+/+ (A) and AnxA1−/− (B) mice were stimulated with plate-bound anti-CD3(1 μg/ml) and anti-CD28 (1 μg/ml) in presence of the indicated concentrations of VJ-4B6. After 18-20 hours, cells were collected and stained with anti-CD25 FITC plus anti-CD69 PE. Samples were acquired by FACScalibur and analyzed by FlowJo software. The data shown are from a single experiment and are representative of other two experiments with similar results.

FIG. 11 shows the DNA (SEQ ID NO:13 and SEQ ID NO:14) and amino acid sequence (SEQ ID NO:15) of the light chain variable region of VJ-4B6.

FIG. 12 shows the amino acid sequence (SEQ ID NO:16) of the light chain variable region of VJ-4B6 with the CDRs annotated. CDR1, CDR2, CDR3 and the beginning of the constant region are highlighted. Numbering and CDRs according to Kabat.

FIG. 13 shows the DNA (SEQ ID NO:17 and SEQ ID NO:18) and amino acid sequence (SEQ ID NO:19) of the heavy chain variable region of VJ-4B6.

FIG. 14 shows the amino acid sequence (SEQ ID NO:20) of the heavy chain variable region of VJ-4B6 with the CDRs annotated. CDR1, CDR2, CDR3 and the beginning of the constant region are highlighted. Numbering and CDRs according to Kabat. In the heavy chain variable region residues 26 to 29, although not part of the hypervariable region as defined by Kabat, are part of the CDR loop defined by Chothia (Chothia and Lesk, 1987). Positions at insertions 52, 52a, 82, 82a, 82b, 82c, 100 and 100a, are indicated as 52a, 82abc, 100a.

FIG. 15 shows that VJ-4B6 inhibits the development of EAE. C57BL/6 mice were immunized with $MOG_{35-55}$ in CFA and monitored daily for signs of EAE for 22 days. At day 6 after the immunization, mice received an i.p. injection of 100 ng of IgG (A) or 5 (B), 50 (C) 100 ng (D) of VJ-4B6 (in 100 μl of PBS) every six days. Results are means±SEM (n=6/group). *p<0.05, ***p<0.001.

FIG. 16 shows that VJ-4B6 reduces the weight loss associated with the development of EAE. C57BL/6 mice were immunized with $MOG_{35-55}$ in CFA and monitored daily for weight gain/loss for 22 days. At day 6 after the immunization, mice received an i.p. injection of 100 ng of IgG (A) or 5 (B), 50 (C) 100 ng (D) of VJ-4B6 (in 100 μl of PBS) every six days. Results are means±SEM (n=6/group). *p<0.05, ***p<0.001.

Figure 17:
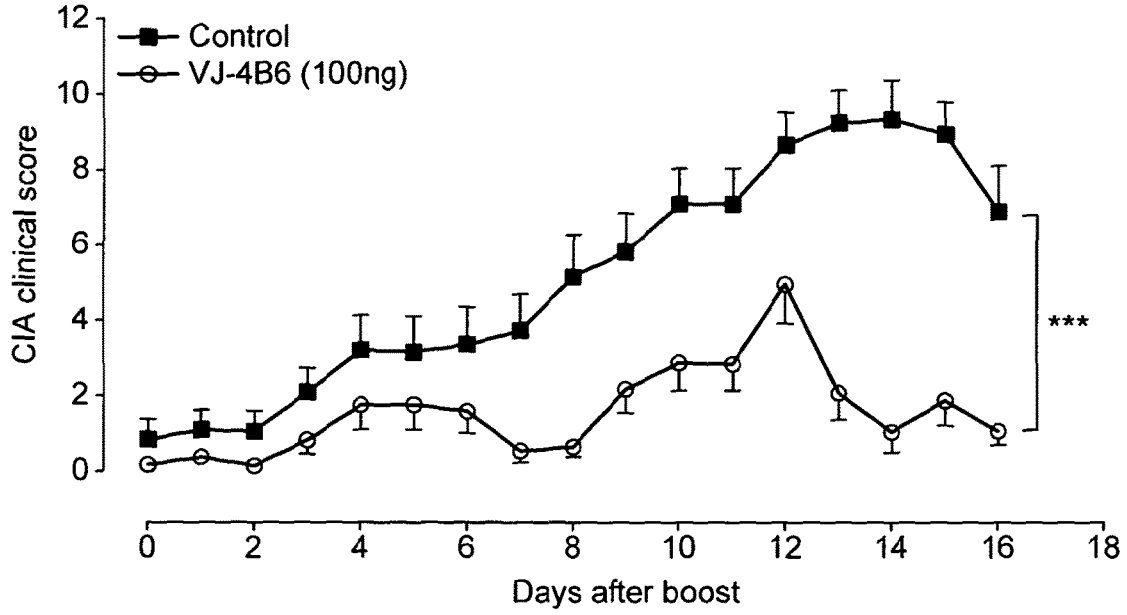

FIG. 17 shows that VJ-4B6 reduces the development of CIA. DBA/1 mice were immunized with bovine type II collagen in CFA. At 21 days after the primary immunization, mice were boosted (s.c.) with 200 μg type II in complete CFA and monitored daily for signs of disease for 20 days. The day of the boosting mice received an i.p. injection of 100 ng of VJ-4B6 (in 100 μl of PBS) every six days. Results are means±SEM (n=6/group). ***p<0.001.

EXAMPLE 1

VJ-4B6 Specifically Inhibits T Cell Activation in Annexin-1 Containing T Cells Materials and Methods Mice (mice used in FIGS. 4B, 5, 6, 7, 8, 9 and 10)

Balb/C mice were obtained from B&K Universal (Grimston, England). $AnxA1^{-/-}$ mice were generated in the inventors' lab and bred in pathogen free conditions at B&K Universal. All mice used in these studies were aged between 6 and 8 weeks. Animal work was performed according to United Kingdom Home Office regulations (Guidance on the Operation of Animals, Scientific Procedures Act 1986) and regulations of the European Union directives.

Murine T Cell Extraction (Cells Used in FIGS. 4B, 5, 6, 7, 8, 9 and 10)

Spleen and lymph nodes (axillary, inguinal and intestinal) were removed from 6 to 8 week old mice and prepared by gentle disaggregation of tissue through a 50 μm cell strainer (BD), with a syringe plunger as previously described. Cell suspensions were layered over Ficoll to obtain the mononuclear cells and then collected and washed with RPMI medium (Gibco).

T Cell Proliferation Assay (Data in FIGS. 5 and 6)

Purified lymph node T cells ($10^5$ cells/ml) were stimulated by plate-bound anti-CD3 (clone 145-2C11; eBioscience) or anti-CD3 plus anti-CD28 (clone 37.51; eBioscience) in 96 well plates. After 18-20 h, cultures were pulsed for 12 h with 1 μCi of [$^3$H]-thymidine (Amersham Pharmacia Biotech) and incorporated radioactivity was measured by automated scintillation counter (Packard).

IL-2 Production (Data in FIGS. 7 and 8)

Purified lymph node T cells ($10^5$ cells/ml) were stimulated by plate-bound anti-CD3 (clone 145-2C11; eBioscience) or anti-CD3 plus anti-CD28 (clone 37.51; eBioscience) in 96 well plates. After 20-24 h, culture supernatants were collected and analyzed for IL-2 content using mouse IL-2 ELISA kit (eBioscience) according to the manufacturer's instructions.

Flow Cytometric Analysis (FIGS. 9 and 10)

Cells were resuspended in FACS buffer (PBS containing 1% FCS and 0.02% $NaN_2$). Lymphocytes were stained at $1\times10^6$/ml in 100 μl of FACS buffer and acquired on a FACScalibur with the CellQuest™ software (Becton Dickinson). The antibodies used were anti-CD25 FITC (clone PC61, eBioscience) and PE-conjugated anti-CD69 (clone H1.2F3). Cells were preincubated in FACS buffer containing anti-CD16/32 for 30 min at 4° C. to avoid non-specific binding and then labeled with the appropriate concentration of conjugated antibodies for 30 minutes at 4° C. After labeling, cells were washed and analyzed. Forward and side scatters were set to exclude erythrocytes and dead cells, and at least $2\times10^4$ lymphocytes were analyzed per sample. In all the experiments stained cells were acquired with a FACScalibur flow cytometer and analyzed using FlowJo software.

Validation of VJ-4B6 by Flow Cytometric Analysis (FIG. 4)

Human PBMC and PMN or murine splenocytes and peritoneal macrophages were resuspended first in FACS buffer containing 4% paraformaldehyde for 10 minutes and thereafter in FACS buffer containing 4% paraformaldehyde and 0.02% saponin for 15 minutes. Cells were incubated with 50 ng/ml of biotinylated VJ-4B6 for 12 hours at 4° C. Thereafter, cells were incubated with streptavidin-FITC (dil.1:200; eBioscience) for 1 hour at room temperature. After labeling, cells were washed and analyzed. Forward and side scatters were set to exclude erythrocytes and dead cells, and at least $2\times10^4$ lymphocytes were analyzed per sample. In all the experiments stained cells were acquired with a FACScalibur flow cytometer and analyzed using FlowJo software.

Figure 4A:
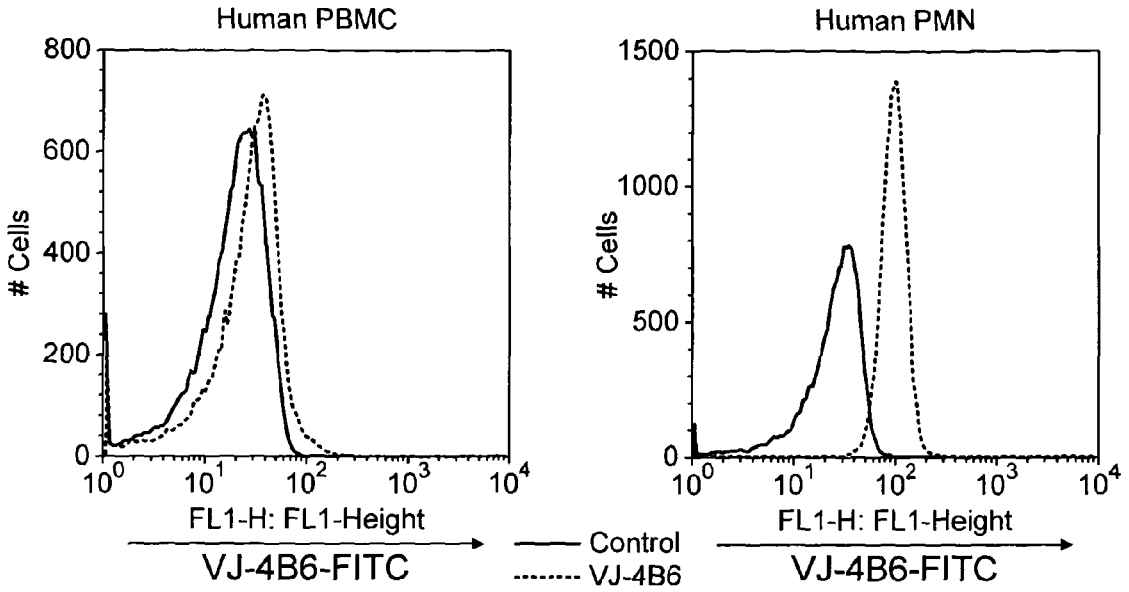
Figure 4B:
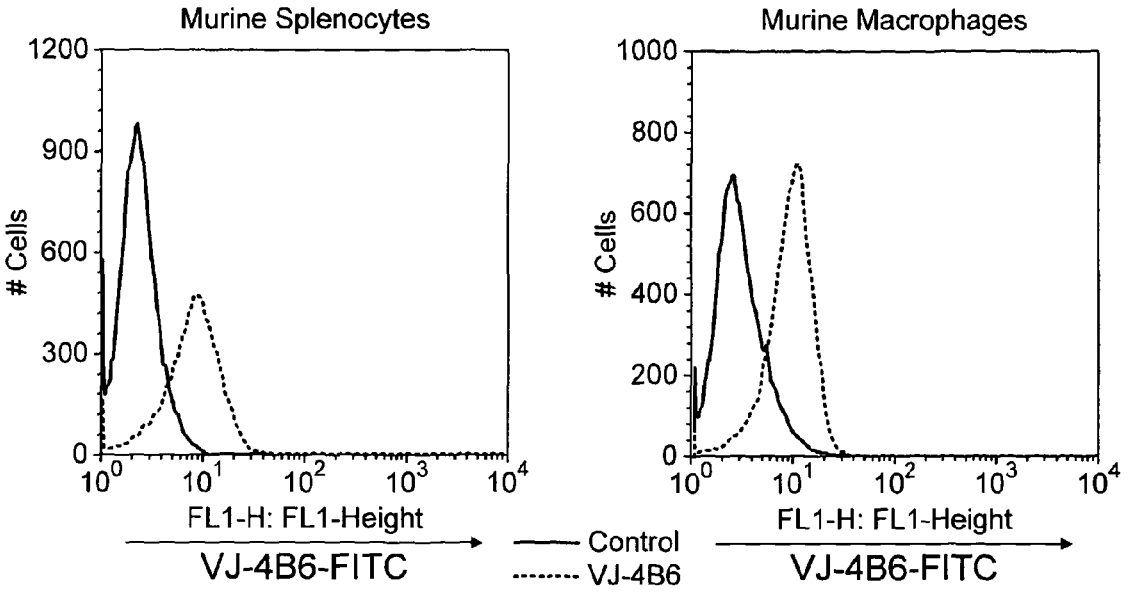

Human Peripheral Blood Leukocytes (Cells Used in FIG. 4A)

Blood donors were 20- to 35-year-old healthy men and women who were tested to be negative for HIV, hepatitis B virus, and hepatitis C virus. Further exclusion criteria were manifest infections during the last 4 weeks, fever, symptomatic allergies, abnormal blood cell counts, increased liver enzymes, or medication of any kind. Fresh venous blood was collected from healthy volunteers and immediately transferred to a tube containing 3.2% sodium citrate (1:10 dilution). Cells were then separated using the density gradient method: 3 ml of Ficoll Histopaque-10771 was layered on top of 3 ml of Ficoll Histopaque-11911 (both from Sigma) to create discrete layers and 6 ml of blood (diluted 1:1 with RPMI medium) layered on top of the Histopaques. After centrifugation at 1500 RPM at room temperature for 30 minutes, PBMCs and PMNs were aspirated from their appropriate layer using a sterile Pasteur pipette and washed with RPMI three times.

Statistical Analysis

All statistical analysis was performed with Prism software (GraphPad software). All values are expressed as mean±SE. Statistical analysis was assessed either by Student's t test or one-way ANOVA where appropriate. A probability of $P<0.05$ was considered significant.

Results

A novel anti-AnxA1 antibody was generated by genetic immunisation as indicated in the scheme in FIG. 3A (Genovac GmbH, Germany). Serum from several immunized mice were tested and three resulted positive for IgG recognizing cells transfected with AnxA1 cDNA. Splenocytes from these mice were fused to myeloma cells to generate hybridoma cells. Only one of the three hybridoma cell clones were successfully subcloned and expanded. These hybridoma cells are called VJ-4B6-E5-B10-D4. Purified IgG2b fraction from the hybridoma cells recognizes cells transfected with AnxA1 cDNA (FIG. 3B, green line; right-hand peak) but not cell transfected with an irrelevant cDNA (FIG. 3B, red line; left-hand peak).

To validate the specificity of VJ-4B6, the expression of AnxA1 in permeabilised human and murine cells known to express different levels of protein was analysed by FACS. As shown in FIG. 4A, human PMN were highly positive for VJ-4B6 staining compared with human PBMC (FIG. 4A, right-hand peak, right and left panel, respectively). This is consistent with previous observations (D'Acquisto et al, unpublished results) that PMN express significantly higher levels of AnxA1 compared to PBMC. Similarly, staining of murine macrophages with VJ-4B6 showed higher levels of expression of AnxA1 compared to splenocytes (FIG. 4B, right-hand peak, right and left panel, respectively). Collectively, these results show that VJ-4B6 recognize both human and murine AnxA1.

Figure 5A:
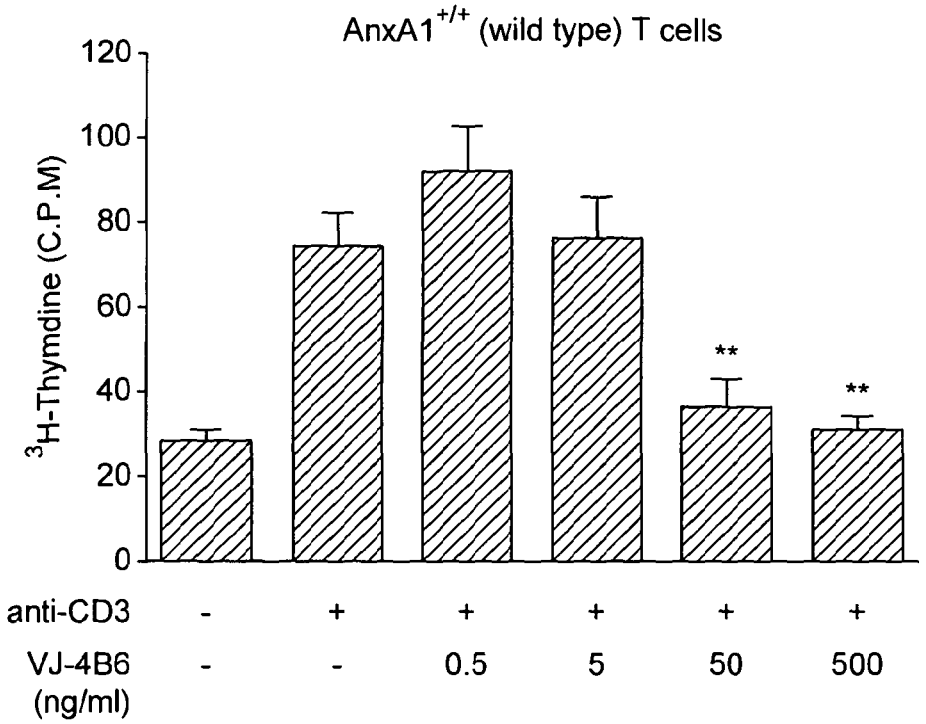
Figure 5B:
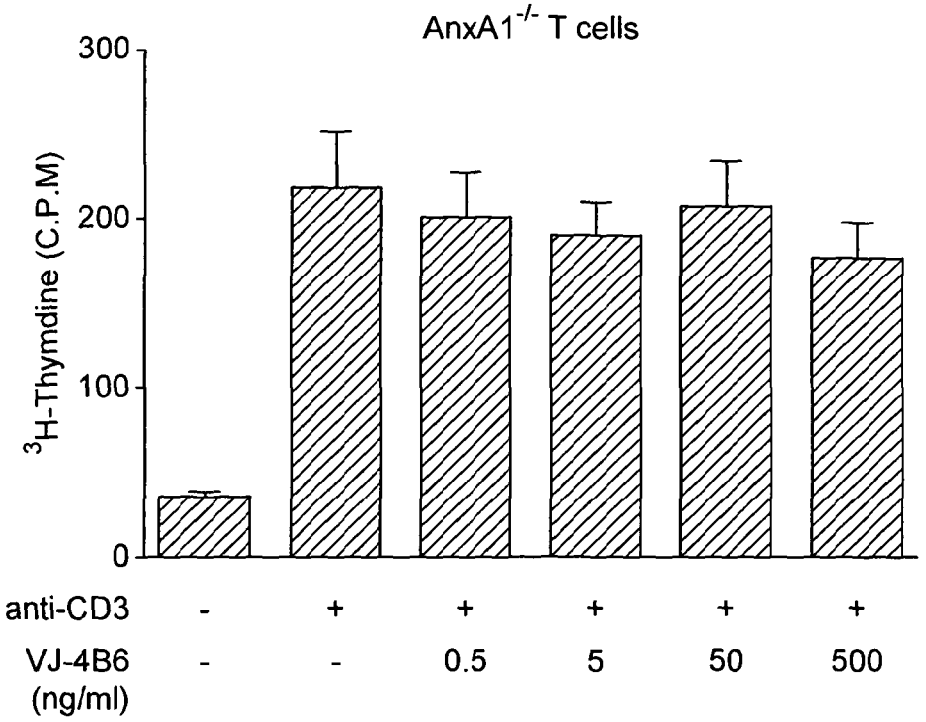
Figure 6A:
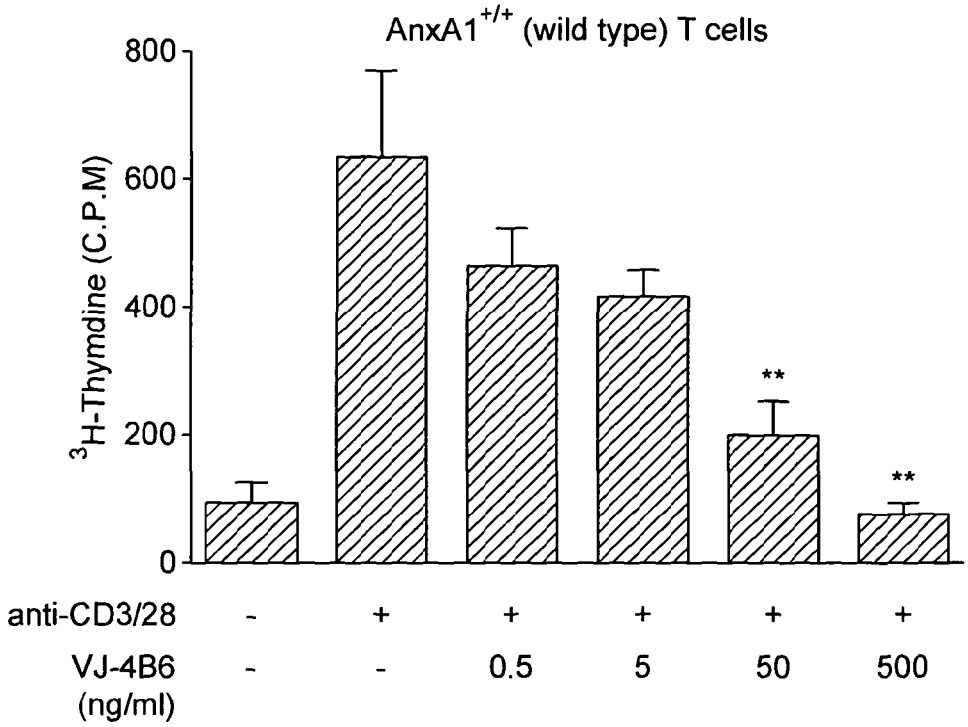
Figure 6B:
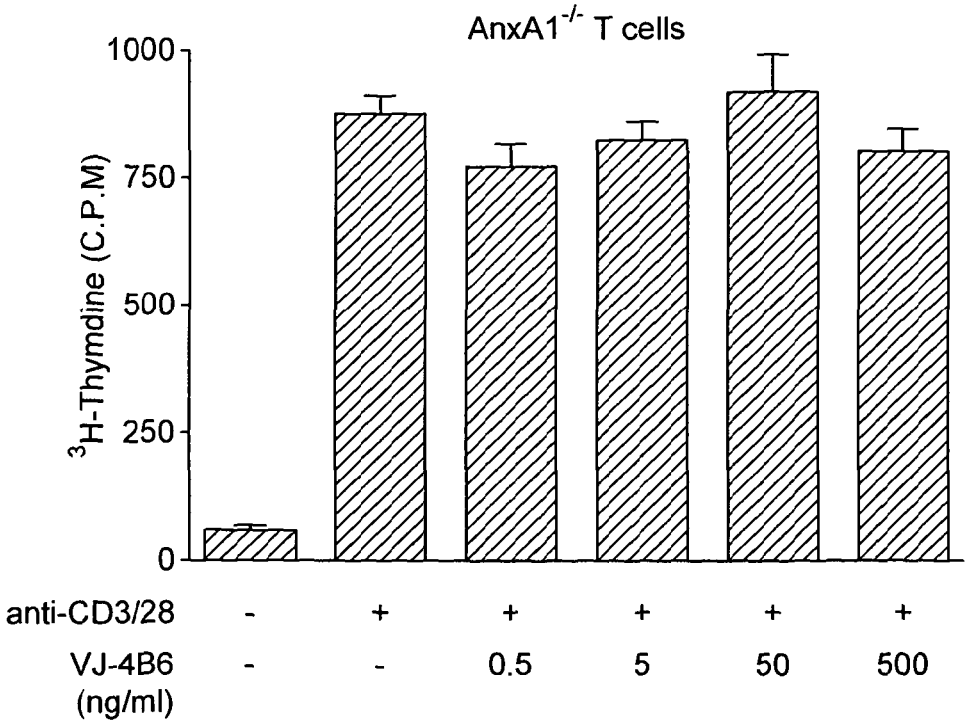

Next, the effects and the specificity of VJ-4B6 on T cell activation were tested. To this aim, first the effects of VJ-4B6 on anti-CD3-induced cell proliferation (as mean of $^3$H-thymidine incorporation) were measured using T cells from $AnxA1^{+/+}$ or $AnxA1^{-/-}$ mice. FIG. 5 shows an increased incorporation of $^3$H-thymidine in both $AnxA1^{+/+}$ and $AnxA1^{-/-}$ T cells following stimulation with anti-CD3 (FIGS. 5A and 5B, respectively). Addition of VJ-4B6 to the stimulated cultures, caused a concentration-dependent inhibition of $^3$H-thymidine incorporation in $AnxA1^{+/+}$ but not $AnxA1^{-/-}$ T cells. Similar results were obtained with T cells stimulated with anti-CD3 plus anti-CD28 (FIGS. 6A and 6B, respectively).

To further confirm these results, the effect of VJ-4B6 on other classical markers of T cell activation, i.e. interleukin-2 (IL-2) production and CD25/CD69 upregulation, were tested. T cells stimulated with either anti-CD3 alone or anti-CD3 plus anti-CD28 produced large amount of IL-2 (FIGS. 7 and 8, respectively). Addition of VJ-4B6 inhibited significantly and in a concentration-dependent manner IL-2 production in $AnxA1^{+/+}$ but not $AnxA1^{-/-}$ T cells. Similar results were obtained on CD25/CD69 upregulation. Activation of T cells with either anti-CD3 alone or anti-CD3 plus anti-CD28 induced a marked increase in the percentage of CD25/CD69 double positive T cells (second panels from the left, FIGS. 9 and 10, respectively). Stimulation in presence of VJ-4B6 inhibited significantly and in a concentration-dependent manner CD25/CD69 induction (and expression) in $AnxA1^{+/+}$ but not $AnxA1^{-/-}$ T cells.

Together these results show that VJ-4B6 significantly inhibits T cell proliferation, IL-2 production and CD25/CD69 upregulation induced by signalling elicited by either anti-CD3 or anti-CD3 plus anti-CD28. In addition this effect is specifically due to the neutralization of AnxA1 by VJ-4B6 since its effect is lost in AnxA1$^{-/-}$ T cells. This is consistent with the inventors' previous observations that activated T cells release endogenous AnxA1 that would be—in turn—required for proper T cell activation (D'Acquisto et al., Blood 109: 1095-1102, 2007; D'Acquisto et a, Eur. J. Immunol. 37: 3131-3142, 2007).

In summary, these data show that VJ-4B6 inhibits anti-CD3-induced upregulation of CD25 and CD69 (markers of T cell activation) in a concentration dependent manner. Similar inhibitory effect was observed on IL-2 production and on T cell proliferation. Most importantly, this effect was not observed in Annexin-1-deficient T cells, demonstrating that the inhibition is specific and that the antibody does not cause any adverse cytotoxic effects.

EXAMPLE 2

Sequencing of VJ-4B6

The aim of this Example was to clone the antibody heavy and light chain variable region genes from the hybridoma cells and to determine the DNA sequence and location of the complementarity determining regions (CDRs) and other features.

Cloning and Sequencing of Antibody Variable Regions

Total RNA was prepared from 1 vial of hybridoma cells using the Qiagen RNeasy mini kit (Cat No: 74104). RNA was eluted in 504, water and checked on a 1.2% agarose gel.

$V_H$ and $V_K$ (variable kappa light chain) cDNAs were prepared using reverse transcriptase with IgG and kappa constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size. The DNA sequence of selected clones was determined in both directions by automated DNA sequencing. The locations of the complementarity determining regions (CDRs) in the sequences were determined with reference to other antibody sequences (Kabat E A et al., 1991).

Results

VJ-4B6 Light Chain

A single $V_K$ sequence was identified. The DNA sequence and deduced amino acid sequence for the VJ-4B6 $V_K$ is shown in FIG. 11. The deduced protein sequence with CDRs annotated is shown in FIG. 12, Nine clones (seven independent) from two separate amplification steps gave identical V region sequence. The non-productive aberrant $V_K$ sequence that arises from the hybridoma fusion partner was also present in a number of clones and there was one clone with a deletion within the sequence.

VJ-4B6 Heavy Chain

A single $V_H$ sequence was identified. The DNA sequence and deduced amino acid sequence for the VJ-4B6 $V_H$ is shown in FIG. 13. The same V region sequence was found in nine independent clones. Two clones had a single base pair change, one clone had a single base pair deletion and a single base pair change, and one clone had two single base pair changes. Each of the five single base pair changes occurred in only one clone. The remaining five clones had identical sequence. The deduced protein sequence with CDRs annotated is shown in FIG. 14.

REFERENCES

Chothia C and Lesk A M. Canonical structures for the hypervariable regions of immunoglobulins. J Mol Biol. 196: 901-17, 1987.

Kabat E A, Wu T T, Perry H M, Gottesman K S, Foeller C. Sequences of proteins of Immunological Interest, US Department of Health and Human Services, 1991

EXAMPLE 3

Immunosuppressive Effects of VJ-4B6 In Vivo

To test the immunosuppressive effects of VJ-4B6 in vivo, we chose two classical models of autoimmune diseases: the $MOG_{33-55}$-induced experimental autoimmune encephalomyelitis (EAE; mouse model of multiple sclerosis) and the collagen-induced arthritis (CIA; mouse model of rheumatoid arthritis).

Methods

Experimental autoimmune encephalomyelitis. Mice were immunized subcutaneously on day 0 with 300 μl of emulsion consisting of 300 μg of $MOG_{35-55}$ in PBS combined with an equal volume of CFA containing 300 μg heat-killed M. tuberculosis H37Ra. The emulsion was injected in both flanks and followed by an intraperitoneal injection of B. pertussis toxin (500 ng/100 μl) in 100 μl of saline on days 0 and 2. Mice were observed daily for signs of EAE and weight loss. Disease severity was scored on a 6-point scale: 0=no disease; 1=partial flaccid tail; 2=complete flaccid tail; 3=impaired righting reflex; 4=partial hind limb paralysis; 5=complete hind limb paralysis; 6=moribund or dead animal.

Figure 15A:
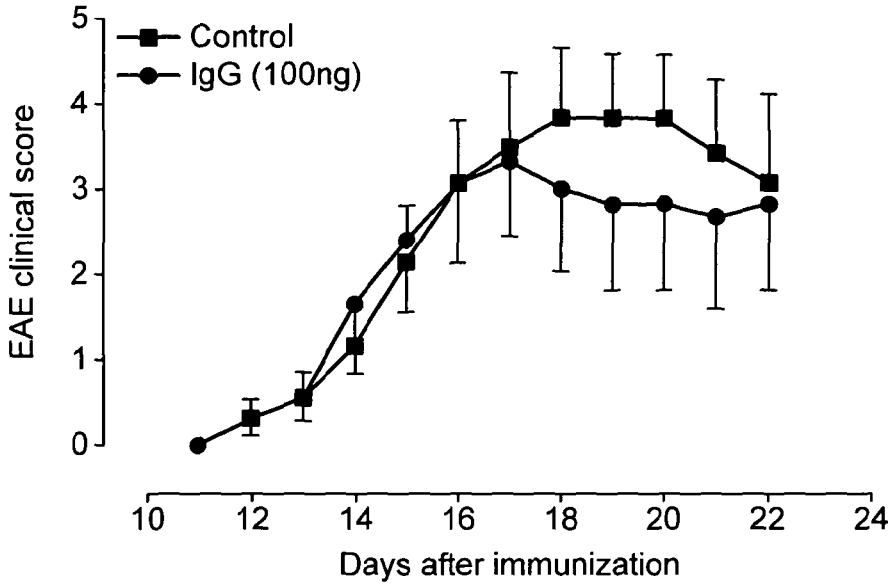
Figure 15B:
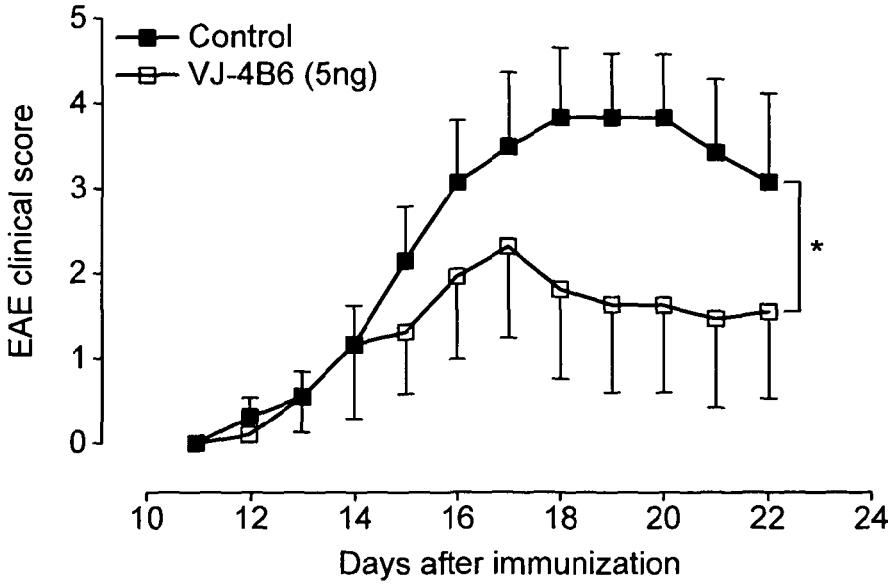
Figure 15C:
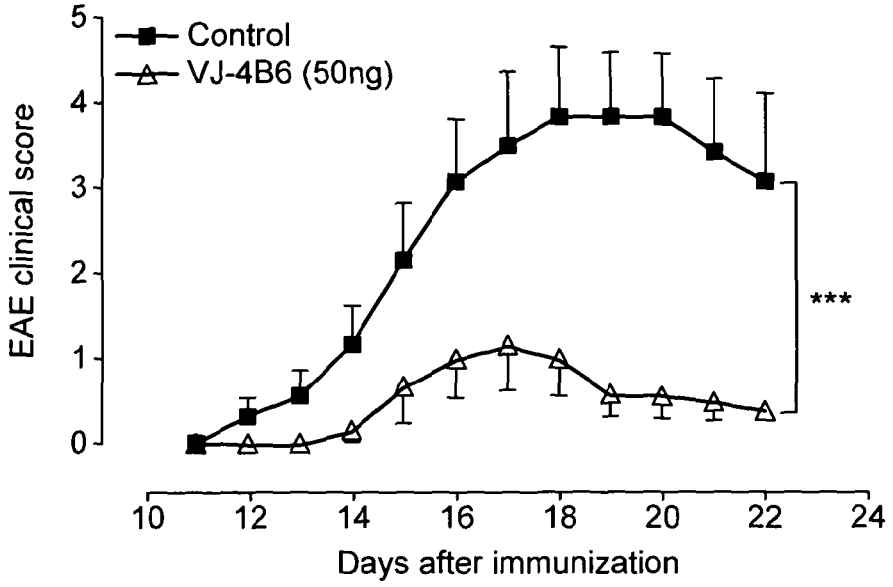
Figure 15D:
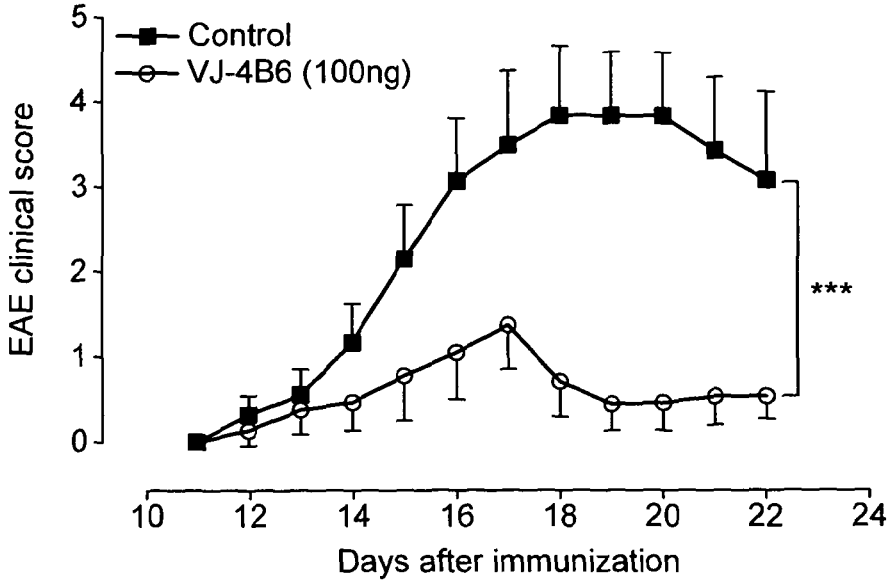
Figure 16A:
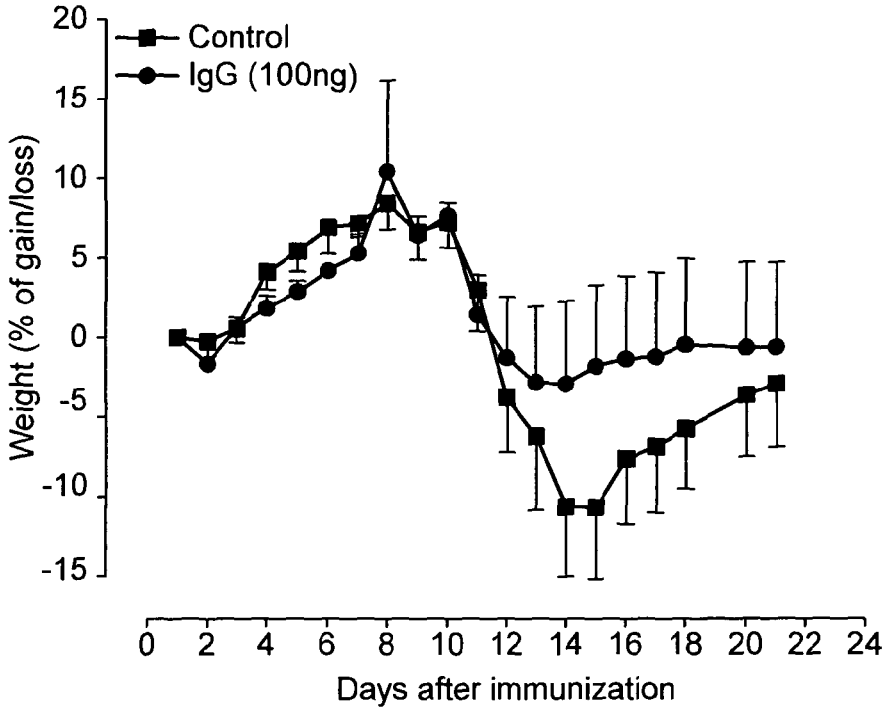
Figure 16B:
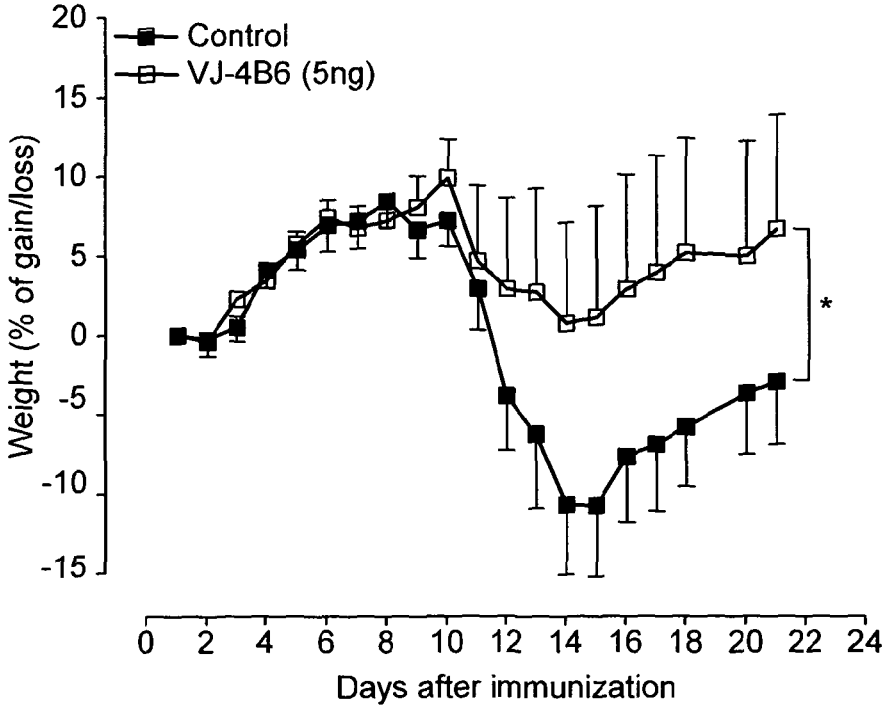
Figure 16C:
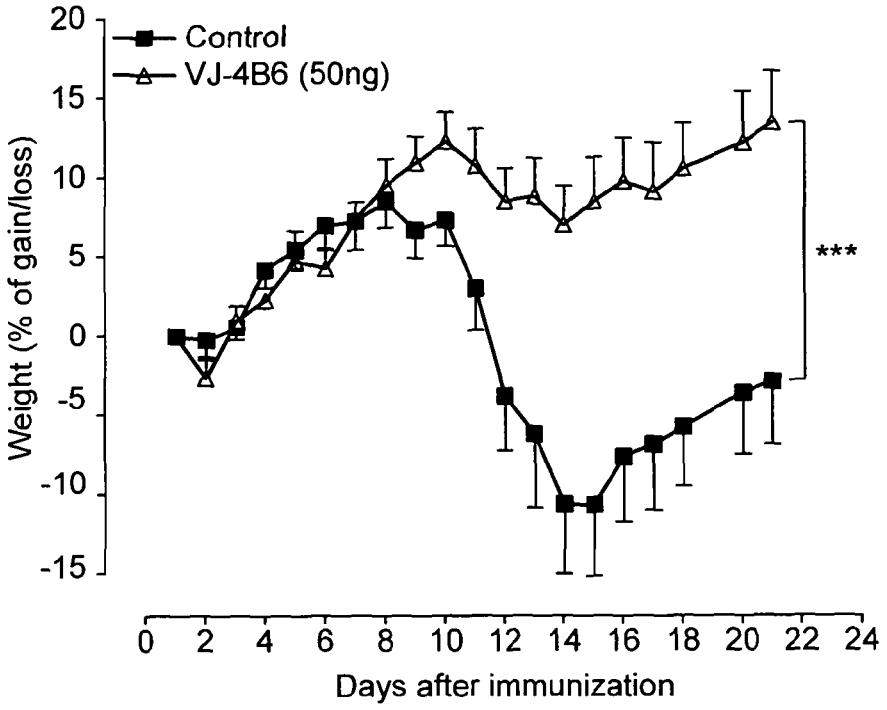
Figure 16D:
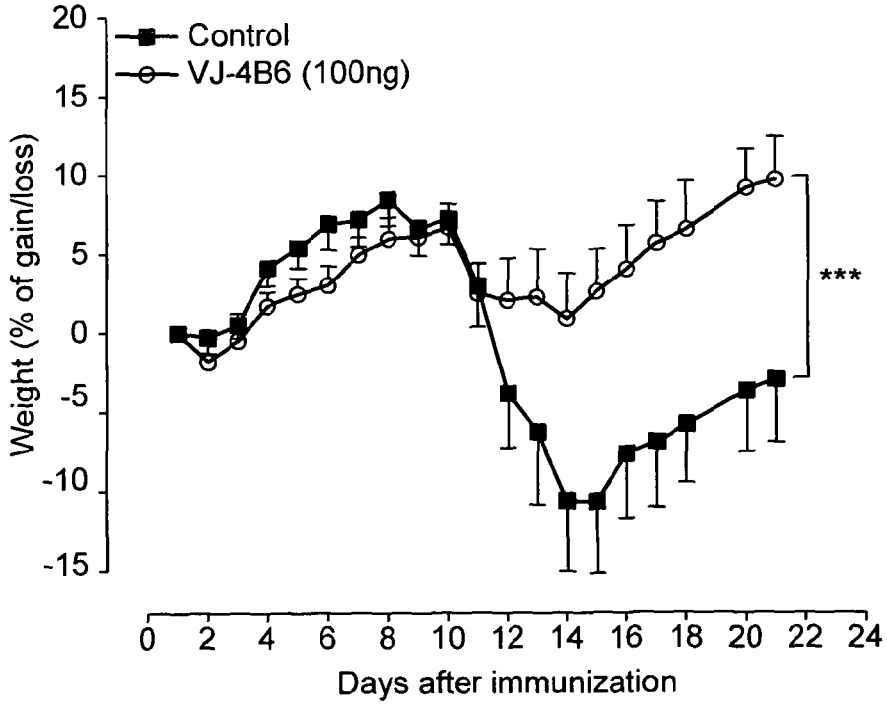

Collagen Induced Arthritis. Six to eight male DBA/1 mice (8-12 weeks old) were injected intradermally at the base of the tail with 200 μg collagen type II emulsified in complete Freund's adjuvant (CFA; Hooke labs). At 21 days after the primary immunization, mice were boosted (s.c.) with 200 μg type II in IFA (Hooke labs). Mice were monitored for signs of arthritis onset using two clinical parameters: paw swelling and clinical score. Paw swelling was assessed by measuring thickness of the affected hind paws with plethysmometer. Clinical arthritis was assessed as recommended by the manufacturer (http://hookelabs.com/protocols/ciaInduction-DBA1/ciaInduction_DBA1.html). Each limb was graded, giving a maximum possible score of 12 per animal Results Male C57/BL6 mice were immunized with $MOG_{33-55}$/CFA as previously described (Paschalidis et al., J Neuroinflammation. 2009; 6:33). Mice received an intraperitoneal (i.p.) administration of VJ-4B6 (5, 50 and 100 ng/100 μl), IgG control (100 ng/μl) or PBS vehicle (control) every six days starting at day 6 after the immunization with $MOG_{33-55}$/CFA. As shown in FIG. 15, mice treated with 5, 50 and 100 ng of VJ-4B6 showed a statistically significant dose-dependent reduction of signs of disease compared with control mice (FIGS. 15B, C and D, respectively) while administration of IgG control had no effects (FIG. 15A). The area under the curve (AUC) for each treatment and the percentage of inhibition versus the control (27.29 AUC) were the following: IgG100 ng, 24.17 AUC, 11.4%; VJ-4B6 5 ng, 15.04 AUC, 44.8%; VJ-4B6 50 ng, 5.87 AUC, 78.5%; VJ-4B6 100 ng, 7.04 AUC, 74.2%.

Studies on animal models of EAE have demonstrated that the acute phase of the disease coincides with weight loss, probably due to anorexia and deficient fluid uptake. Weight measurement of treated mice correlated with the severity of the clinical score and showed a dose-dependent reduced weight loss—from day 18 onwards—in the VJ-4B6-treated but not IgG-treated mice compared to controls (FIG. 16).

To confirm the therapeutic potential of VJ-4B6 as immunosuppressant in vivo, we tested its effects in the CIA model. Male DBA/1 mice were immunized with bovine type II collagen in CFA as previously described (D'Acquisto et al., Blood. 2007; 109(3):1095-102). Mice received an i.p. injection of VJ-4B6 (100 ng/100 μl) or PBS vehicle (control) every six days starting at day 0 after the boost with collagen. Consistent with the data obtained on the EAE, administration of VJ-4B6 significantly reduced (AUC 26.75; 67.9%) the development of sign of disease compared to control mice (AUC 83.50) (FIG. 17).

SEQUENCE LISTING

```
<160> NUMBER OF SEQ ID NOS: 20

<210> SEQ ID NO 1
<211> LENGTH: 25
<212> TYPE: PRT
<213> ORGANISM: Homo sapiens
<220> FEATURE:
<221> NAME/KEY: ACETYLATION
<222> LOCATION: (1)..(1)

<400> SEQUENCE: 1

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25


<210> SEQ ID NO 2

<400> SEQUENCE: 2

000


<210> SEQ ID NO 3

<400> SEQUENCE: 3

000


<210> SEQ ID NO 4

<400> SEQUENCE: 4

000


<210> SEQ ID NO 5
<211> LENGTH: 10
<212> TYPE: PRT
<213> ORGANISM: Unknown
<220> FEATURE:
<223> OTHER INFORMATION: VHCDR1

<400> SEQUENCE: 5

Gly Tyr Thr Phe Thr Asn Tyr Trp Ile Gly
1               5                   10


<210> SEQ ID NO 6
<211> LENGTH: 17
<212> TYPE: PRT
<213> ORGANISM: Unknown
<220> FEATURE:
<223> OTHER INFORMATION: VHCDR2

<400> SEQUENCE: 6

Asp Ile Tyr Pro Gly Gly Asp Tyr Thr Asn Tyr Asn Glu Lys Phe Lys
1               5                   10                  15

Gly


<210> SEQ ID NO 7
<211> LENGTH: 9
<212> TYPE: PRT
```

<213> ORGANISM: Unknown
<220> FEATURE:
<223> OTHER INFORMATION: VHCDR3

<400> SEQUENCE: 7

Trp Gly Leu Gly Tyr Tyr Phe Asp Tyr
1 5

<210> SEQ ID NO 8
<211> LENGTH: 346
<212> TYPE: PRT
<213> ORGANISM: Homo sapiens

<400> SEQUENCE: 8

Met Ala Met Val Ser Glu Phe Leu Lys Gln Ala Trp Phe Ile Glu Asn
1 5 10 15

Glu Glu Gln Glu Tyr Val Gln Thr Val Lys Ser Ser Lys Gly Gly Pro
20 25 30

Gly Ser Ala Val Ser Pro Tyr Pro Thr Phe Asn Pro Ser Ser Asp Val
35 40 45

Ala Ala Leu His Lys Ala Ile Met Val Lys Gly Val Asp Glu Ala Thr
50 55 60

Ile Ile Asp Ile Leu Thr Lys Arg Asn Asn Ala Gln Arg Gln Gln Ile
65 70 75 80

Lys Ala Ala Tyr Leu Gln Glu Thr Gly Lys Pro Leu Asp Glu Thr Leu
85 90 95

Lys Lys Ala Leu Thr Gly His Leu Glu Glu Val Val Leu Ala Leu Leu
100 105 110

Lys Thr Pro Ala Gln Phe Asp Ala Asp Glu Leu Arg Ala Ala Met Lys
115 120 125

Gly Leu Gly Thr Asp Glu Asp Thr Leu Ile Glu Ile Leu Ala Ser Arg
130 135 140

Thr Asn Lys Glu Ile Arg Asp Ile Asn Arg Val Tyr Arg Glu Glu Leu
145 150 155 160

Lys Arg Asp Leu Ala Lys Asp Ile Thr Ser Asp Thr Ser Gly Asp Phe
165 170 175

Arg Asn Ala Leu Leu Ser Leu Ala Lys Gly Asp Arg Ser Glu Asp Phe
180 185 190

Gly Val Asn Glu Asp Leu Ala Asp Ser Asp Ala Arg Ala Leu Tyr Glu
195 200 205

Ala Gly Glu Arg Arg Lys Gly Thr Asp Val Asn Val Phe Asn Thr Ile
210 215 220

Leu Thr Thr Arg Ser Tyr Pro Gln Leu Arg Arg Val Phe Gln Lys Tyr
225 230 235 240

Thr Lys Tyr Ser Lys His Asp Met Asn Lys Val Leu Asp Leu Glu Leu
245 250 255

Lys Gly Asp Ile Glu Lys Cys Leu Thr Ala Ile Val Lys Cys Ala Thr
260 265 270

Ser Lys Pro Ala Phe Phe Ala Glu Lys Leu His Gln Ala Met Lys Gly
275 280 285

Val Gly Thr Arg His Lys Ala Leu Ile Arg Ile Met Val Ser Arg Ser
290 295 300

Glu Ile Asp Met Asn Asp Ile Lys Ala Phe Tyr Gln Lys Met Tyr Gly
305 310 315 320

Ile Ser Leu Cys Gln Ala Ile Leu Asp Glu Thr Lys Gly Asp Tyr Glu
325 330 335

Lys Ile Leu Val Ala Leu Cys Gly Gly Asn
340 345

<210> SEQ ID NO 9
<211> LENGTH: 1041
<212> TYPE: DNA
<213> ORGANISM: Homo sapiens

<400> SEQUENCE: 9 atggcaatgg tatcagaatt cctcaagcag gcctggttta ttgaaaatga agagcaggaa 60 tatgttcaaa ctgtgaagtc atccaaaggt ggtcccggat cagcggtgag cccctatcct 120 accttcaatc catcctcgga tgtcgctgcc ttgcataagg ccataatggt taaaggtgtg 180 gatgaagcaa ccatcattga cattctaact aagcgaaaca atgcacagcg tcaacagatc 240 aaagcagcat atctccagga aacaggaaag cccctggatg aaacactgaa gaaagccctt 300 acaggtcacc ttgaggaggt tgttttggct ctgctaaaaa ctccagcgca atttgatgct 360 gatgaacttc gtgctgccat gaagggcctt ggaactgatg aagatactct aattgagatt 420 ttggcatcaa gaactaacaa agaaatcaga gacattaaca gggtctacag agaggaactg 480 aagagagatc tggccaaaga cataacctca gacacatctg gagattttcg gaacgctttg 540 ctttctcttg ctaagggtga ccgatctgag gactttggtg tgaatgaaga cttggctgat 600 tcagatgcca gggccttgta tgaagcagga gaaaggagaa aggggacaga cgtaaacgtg 660 ttcaatacca tccttaccac cagaagctat ccacaacttc gcagagtgtt tcagaaatac 720 accaagtaca gtaagcatga catgaacaaa gttctggacc tggagttgaa aggtgacatt 780 gagaaatgcc tcacagctat cgtgaagtgc gccacaagca aaccagcttt ctttgcagag 840 aagcttcatc aagccatgaa aggtgttgga actcgccata aggcattgat caggattatg 900 gtttcccgtt ctgaaattga catgaatgat atcaaagcat tctatcagaa gatgtatggt 960 atctcccttt gccaagccat cctggatgaa accaaaggag attatgagaa aatcctggtg 1020 gctctttgtg gaggaaacta a 1041

<210> SEQ ID NO 10
<211> LENGTH: 346
<212> TYPE: PRT
<213> ORGANISM: Homo sapiens

<400> SEQUENCE: 10

Met Ala Met Val Ser Glu Phe Leu Lys Gln Ala Trp Phe Ile Glu Asn
1 5 10 15

Glu Glu Gln Glu Tyr Val Gln Thr Val Lys Ser Ser Lys Gly Gly Pro
20 25 30

Gly Ser Ala Val Ser Pro Tyr Pro Thr Phe Asn Pro Ser Ser Asp Val
35 40 45

Ala Ala Leu His Lys Ala Ile Met Val Lys Gly Val Asp Glu Ala Thr
50 55 60

Ile Ile Asp Ile Leu Thr Lys Arg Asn Asn Ala Gln Arg Gln Gln Ile
65 70 75 80

Lys Ala Ala Tyr Leu Gln Glu Thr Gly Lys Pro Leu Asp Glu Thr Leu
85 90 95

Lys Lys Ala Leu Thr Gly His Leu Glu Glu Val Val Leu Ala Leu Leu
100 105 110

Lys Thr Pro Ala Gln Phe Asp Ala Asp Glu Leu Arg Ala Ala Met Lys
115 120 125

```
Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345


<210> SEQ ID NO 11
<211> LENGTH: 204
<212> TYPE: PRT
<213> ORGANISM: Homo sapiens

<400> SEQUENCE: 11

Met Asn Leu Ile Leu Arg Tyr Thr Phe Ser Lys Met Ala Met Val Ser
1               5                   10                  15

Glu Phe Leu Lys Gln Ala Trp Phe Ile Glu Asn Glu Glu Gln Glu Tyr
            20                  25                  30

Val Gln Thr Val Lys Ser Ser Lys Gly Gly Pro Gly Ser Ala Val Ser
        35                  40                  45

Pro Tyr Pro Thr Phe Asn Pro Ser Ser Asp Val Ala Ala Leu His Lys
    50                  55                  60

Ala Ile Met Val Lys Gly Val Asp Glu Ala Thr Ile Ile Asp Ile Leu
65                  70                  75                  80

Thr Lys Arg Asn Asn Ala Gln Arg Gln Gln Ile Lys Ala Ala Tyr Leu
                85                  90                  95

Gln Glu Thr Gly Lys Pro Leu Asp Glu Thr Leu Lys Lys Ala Leu Thr
            100                 105                 110

Gly His Leu Glu Glu Val Val Leu Ala Leu Leu Lys Thr Pro Ala Gln
        115                 120                 125

Phe Asp Ala Asp Glu Leu Arg Ala Ala Met Lys Gly Leu Gly Thr Asp
    130                 135                 140

Glu Asp Thr Leu Ile Glu Ile Leu Ala Ser Arg Thr Asn Lys Glu Ile
```

```
145                 150                 155                 160

Arg Asp Ile Asn Arg Val Tyr Arg Glu Glu Leu Lys Arg Asp Leu Ala
                165                 170                 175

Lys Asp Ile Thr Ser Asp Thr Ser Gly Asp Phe Arg Asn Ala Leu Leu
            180                 185                 190

Ser Leu Ala Lys Gly Asp Arg Ser Glu Asp Phe Gly
        195                 200


<210> SEQ ID NO 12
<211> LENGTH: 115
<212> TYPE: PRT
<213> ORGANISM: Homo sapiens

<400> SEQUENCE: 12

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro
        115


<210> SEQ ID NO 13
<211> LENGTH: 321
<212> TYPE: DNA
<213> ORGANISM: Artificial
<220> FEATURE:
<223> OTHER INFORMATION: light chain variable region of VJ-4B6

<400> SEQUENCE: 13

aacattgtaa tgacccaatc tcccaaatcc atgtccatgt cagtaggaga gagggtcacc     60

ttgacctgca aggccagtga gaatgtggtt acttatgttt cctggtatca acagaaacca    120

gagcagtctc ctaaactgct gatatacggg gcatccaacc ggtacactgg ggtccccgat    180

cgcttcacag gcagtggatc tgcaacagat ttcactctga ccatcagcag tgtgcaggct    240

gaagaccttg cagattatca ctgtggacag ggttacagct atccgtacac gttcggaggg    300

gggaccaagc tggaaataaa a                                              321


<210> SEQ ID NO 14
<211> LENGTH: 321
<212> TYPE: DNA
<213> ORGANISM: Artificial
<220> FEATURE:
<223> OTHER INFORMATION: anti-sense of light chain variable region of
      VJ-4B6

<400> SEQUENCE: 14

ttgtaacatt actgggttag agggtttagg tacaggtaca gtcatcctct ctcccagtgg     60

aactggacgt tccggtcact cttacaccaa tgaatacaaa ggaccatagt tgtctttggt    120
```

```
ctcgtcagag gatttgacga ctatatgccc cgtaggttgg ccatgtgacc ccaggggcta    180

gcgaagtgtc cgtcacctag acgttgtcta aagtgagact ggtagtcgtc acacgtccga    240

cttctggaac gtctaatagt gacacctgtc ccaatgtcga taggcatgtg caagcctccc    300

ccctggttcg acctttattt t                                              321


<210> SEQ ID NO 15
<211> LENGTH: 107
<212> TYPE: PRT
<213> ORGANISM: Artificial
<220> FEATURE:
<223> OTHER INFORMATION: amino acid sequence of the light chain variable
      region of VJ-4B6

<400> SEQUENCE: 15

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105


<210> SEQ ID NO 16
<211> LENGTH: 115
<212> TYPE: PRT
<213> ORGANISM: Artificial
<220> FEATURE:
<223> OTHER INFORMATION: amino acid sequence of light chain variable
      region of VJ-4B6

<400> SEQUENCE: 16

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val
        115


<210> SEQ ID NO 17
<211> LENGTH: 354
```

<212> TYPE: DNA
<213> ORGANISM: Artificial
<220> FEATURE:
<223> OTHER INFORMATION: heavy chain variable region of VJ-4B6

<400> SEQUENCE: 17 caggtccagc tgcagcagtc tggacctgaa ctggtcaggc ctgggacttc agtgaagatg 60 tcctgcaagg cttctggata caccttcact aactactgga taggttgggc aaagcagagg 120 cctggacatg gccttgagtg gattggagat atttaccctg gaggtgatta tactaactac 180 aatgagaagt tcaagggcaa ggccacactg actgcagaca aatcctccag cacagcctac 240 atgcagttca gcagcctgac atctgaggac tctgccatct attattgtgc aagatggggg 300 ttaggatact actttgacta ctggggccaa ggcatcactc tcacagtctc ctca 354

<210> SEQ ID NO 18
<211> LENGTH: 354
<212> TYPE: DNA
<213> ORGANISM: Artificial
<220> FEATURE:
<223> OTHER INFORMATION: anti sense of heavy chain variable region of
VJ-4B6

<400> SEQUENCE: 18 gtccaggtcg acgtcgtcag acctggactt gaccagtccg gaccctgaag tcacttctac 60 aggacgttcc gaagacctat gtggaagtga ttgatgacct atccaacccg tttcgtctcc 120 ggacctgtac cggaactcac ctaacctcta taaatgggac ctccactaat atgattgatg 180 ttactcttca agttcccgtt ccggtgtgac tgacgtctgt ttaggaggtc gtgtcggatg 240 tacgtcaagt cgtcggactg tagactcctg agacggtaga taataacacg ttctaccccc 300 aatcctatga tgaaactgat gaccccggtt ccgtagtgag agtgtcagag gagt 354

<210> SEQ ID NO 19
<211> LENGTH: 118
<212> TYPE: PRT
<213> ORGANISM: Artificial
<220> FEATURE:
<223> OTHER INFORMATION: amino acid sequence of heavy chain variable
region of VJ-4B6

<400> SEQUENCE: 19

Gln Val Gln Leu Gln Gln Ser Gly Pro Glu Leu Val Arg Pro Gly Thr
1 5 10 15

Ser Val Lys Met Ser Cys Lys Ala Ser Gly Tyr Thr Phe Thr Asn Tyr
20 25 30

Trp Ile Gly Trp Ala Lys Gln Arg Pro Gly His Gly Leu Glu Trp Ile
35 40 45

Gly Asp Ile Tyr Pro Gly Gly Asp Tyr Thr Asn Tyr Asn Glu Lys Phe
50 55 60

Lys Gly Lys Ala Thr Leu Thr Ala Asp Lys Ser Ser Ser Thr Ala Tyr
65 70 75 80

Met Gln Phe Ser Ser Leu Thr Ser Glu Asp Ser Ala Ile Tyr Tyr Cys
85 90 95

Ala Arg Trp Gly Leu Gly Tyr Tyr Phe Asp Tyr Trp Gly Gln Gly Ile
100 105 110

Thr Leu Thr Val Ser Ser
115

<210> SEQ ID NO 20

-continued

```
<211> LENGTH: 123
<212> TYPE: PRT
<213> ORGANISM: Artificial
<220> FEATURE:
<223> OTHER INFORMATION: amino acid sequence of heavy chain variable
      region of VJ-4B6

<400> SEQUENCE: 20

Gln Val Gln Leu Gln Gln Ser Gly Pro Glu Leu Val Arg Pro Gly Thr
1               5                   10                  15

Ser Val Lys Met Ser Cys Lys Ala Ser Gly Tyr Thr Phe Thr Asn Tyr
            20                  25                  30

Trp Ile Gly Trp Ala Lys Gln Arg Pro Gly His Gly Leu Glu Trp Ile
        35                  40                  45

Gly Asp Ile Tyr Pro Gly Gly Asp Tyr Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Arg Trp Gly Leu Gly Tyr Tyr Phe Asp Tyr Trp Gly Gln Gly Ile
            100                 105                 110

Thr Leu Thr Val Ser Ser Ala Lys Thr Thr Pro
        115                 120
```

The invention claimed is:

1. An antibody or fragment thereof that binds human Anx-A1 having the amino acid sequence of SEQ ID NO:8, [said antibody or fragment thereof] comprising Complementarity Determining Regions (CDRs) VLCDR1, VLCDR2, VLCDR3, VHCDR1, VHCDR2 and VHCDR3[, each having a respective amino acid sequence as follows in which

| | |
|---|---|
| VLCDR1 is KASENVVTYVS | (SEQ ID NO:2) |
| VLCDR2 is GASNRYT | (SEQ ID NO:3) |
| VLCDR3 is GQGYSYPYT | (SEQ ID NO:4) |
| VHCDR1 is GYTFTNYWIG | (SEQ ID NO:5) |
| VHCDR2 is DIYPGGDYTNYNEKFKG | (SEQ ID NO:6) |
| VHCDR3 is WGLGYYFDY | (SEQ ID NO:7)**]** |

*of an antibody produced by the hybridoma cell line deposited with the European Collection of Cell Cultures (ECACC) on 3 Jun. 2010 as Accession No. 10060301.*

2. An antibody or fragment thereof as claimed in claim 1 wherein the antibody is a monoclonal antibody.

3. An antibody or fragment thereof as claimed in claim 2 wherein the monoclonal antibody is humanized.

4. An antibody or fragment thereof as claimed in claim 1 wherein the fragment is a Fab, $F(ab')_2$ or Fv fragment or an scFv molecule.

5. An antibody or fragment thereof as claimed in claim 1 comprising a heavy chain variable region having the amino acid sequence of SEQ ID NO:19 and/or a light chain variable region having the amino acid sequence of SEQ ID NO:15.

6. An antibody or fragment thereof as claimed in claim 1 produced by the hybridoma cell line deposited with the European Collection of Cell Cultures (ECACC) on 3 Jun. 2010 as Accession No. 10060301, *wherein the antibody is a humanized monoclonal antibody.*

7. A hybridoma cell line which produces an antibody [or fragment thereof] that binds the human Anx-A1 protein having the amino acid sequence of SEQ ID NO:8, [said antibody or fragment thereof comprising] *wherein the antibody comprises* Complementarity Determining Regions (CDRs) VLCDR1, VLCDR2, VLCDR3, VHCDR1, VHCDR2 and VHCDR3[, each having a respective amino acid sequence as follows in which

| | |
|---|---|
| VLCDR1 is KASENVVTYVS, | (SEQ ID NO:2) |
| VLCDR2 is GASNRYT, | (SEQ ID NO:3) |
| VLCDR3 is GQGYSYPYT, | (SEQ ID NO:4) |
| VHCDR1 is GYTFTNYWIG, | (SEQ ID NO:5) |
| VHCDR2 is DIYPGGDYTNYNEKFKG, and | (SEQ ID NO:6) |
| VHCDR3 is WGLGYYFDY | (SEQ ID NO:7)**]** |

*of an antibody produced by the hybridoma cell line deposited with the European Collection of Cell Cultures (ECACC) on 3 Jun. 2010 as Accession No. 10060301.*

[8. A hybridoma cell line as claimed in claim 7 deposited with the European Collection of Cell Cultures (ECACC) on 3 Jun. 2010 as Accession No. 10060301.]

9. A pharmaceutical composition comprising an antibody or fragment thereof as claimed in claim 1.

10. A pharmaceutical composition as claimed in claim 9, further comprising another therapeutically active agent.

*11. An antibody or fragment thereof as claimed in claim 1, wherein the antibody comprises:*

*a light chain variable region produced by the hybridoma cell line deposited with the European Collection of Cell Cultures (ECACC) on 3 Jun. 2010 as Accession No. 10060301; and*

*a heavy chain variable region comprising Complementarity Determining Regions (CDRs) VHCDR1, VHCDR2 and VHCDR3, each having a respective amino acid sequence as follows in which:*

*VHCDR1 is GYTFTNYWIG (SEQ ID NO:5),*

*VHCDR2 is DIYPGGDYTNYNEKFKG (SEQ ID NO:6), and*

*VHCDR3 is WGLGYYFDY (SEQ ID NO:7).*

*12. A humanized antibody comprising the fragment of the antibody as claimed in claim 11, wherein the fragment comprises the CDRs of the antibody defined in claim 11.*

*13. A hybridoma cell line as claimed in claim 7, wherein the antibody comprises:*

*a light chain variable region produced by the hybridoma cell line deposited with the European Collection of Cell Cultures (ECACC) on 3 Jun. 2010 as Accession No. 10060301; and*

*a heavy chain variable region comprising Complementarity Determining Regions (CDRs) VHCDR1, VHCDR2 and VHCDR3, each having a respective amino acid sequence as follows in which:*

*VHCDR1 is GYTFTNYWIG (SEQ ID NO:5),*

*VHCDR2 is DIYPGGDYTNYNEKFKG (SEQ ID NO:6), and*

*VHCDR3 is WGLGYYFDY (SEQ ID NO:7).*

* * * * *